US011241424B2

(12) United States Patent
Li et al.

(10) Patent No.: US 11,241,424 B2
(45) Date of Patent: *Feb. 8, 2022

(54) PHARMACEUTICAL FORMULATIONS FOR SUSTAINED RELEASE OF SEBACOYL DINALBUPHINE ESTER

(71) Applicants: LUMOSA THERAPEUTICS CO., LTD., Taipei (TW); SHANGHAI LUMOSA THERAPEUTICS CO., LTD., Shanghai (CN)

(72) Inventors: Chan-Jung Li, Taipei (TW); David Chih-Kuang Chou, Palo Alto, CA (US); Jin-Ding Huang, Taipei (TW); Shin-Jr Tsai, New Taipei (TW); Shu-Wen Kuo, Taipei (TW); Yu-En Tien, Taipei (TW)

(73) Assignees: Lumosa Therapeutics Co., Ltd., Taipei (TW); Shanghai Lumosa Therapeutics Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/730,020

(22) Filed: Dec. 30, 2019

(65) Prior Publication Data

US 2020/0179372 A1    Jun. 11, 2020

Related U.S. Application Data

(63) Continuation of application No. 16/195,187, filed on Nov. 19, 2018, which is a continuation of application No. 15/166,403, filed on May 27, 2016, now Pat. No. 10,183,018, which is a continuation-in-part of application No. 14/723,996, filed on May 28, 2015, now abandoned.

(60) Provisional application No. 62/255,805, filed on Nov. 16, 2015.

(51) Int. Cl.
*A61K 31/485* (2006.01)
*A61K 47/44* (2017.01)
*A61K 47/14* (2017.01)
*A61K 9/00* (2006.01)

(52) U.S. Cl.
CPC .......... *A61K 31/485* (2013.01); *A61K 9/0019* (2013.01); *A61K 47/14* (2013.01); *A61K 47/44* (2013.01)

(58) Field of Classification Search
CPC ...... A61K 31/485; A61K 47/14; A61K 47/44; A61K 9/0019; A61K 47/10; A61K 9/08
See application file for complete search history.

(56) References Cited

U.S. PATENT DOCUMENTS

| | | |
|---|---|---|
| 4,181,721 A * | 1/1980 | Speck ................ A61K 9/0019 514/178 |
| 6,197,344 B1 | 3/2001 | Chang et al. |
| 6,225,321 B1 | 5/2001 | Hu et al. |
| 6,703,398 B2 | 3/2004 | Hu et al. |
| 8,383,152 B2 | 2/2013 | Jans et al. |
| 8,455,508 B2 | 6/2013 | Luangdilok et al. |
| 8,637,538 B1 | 1/2014 | Sciascia |
| 2003/0105120 A1 | 6/2003 | Hu et al. |
| 2004/0171631 A1 | 9/2004 | Hu et al. |
| 2008/0085304 A1 | 4/2008 | Baichwal et al. |
| 2009/0202634 A1 | 8/2009 | Jans et al. |
| 2011/0038930 A1 | 2/2011 | Barnscheid et al. |
| 2012/0059065 A1 | 3/2012 | Barnscheid et al. |
| 2012/0065220 A1 | 3/2012 | Barnscheid et al. |
| 2013/0028972 A1 | 1/2013 | Schwier et al. |
| 2013/0209557 A1 | 8/2013 | Barnscheid |
| 2013/0225625 A1 | 8/2013 | Barnscheid et al. |
| 2013/0225697 A1 | 8/2013 | Barnscheid et al. |
| 2013/0251759 A1 | 9/2013 | Jans et al. |
| 2013/0273162 A1 | 10/2013 | Li et al. |
| 2013/0280338 A1 | 10/2013 | Wening et al. |
| 2014/0093871 A1 | 4/2014 | Shieh et al. |
| 2014/0112957 A1 | 4/2014 | Hu |
| 2014/0171459 A1 | 6/2014 | Sciascia |
| 2014/0179727 A1 | 6/2014 | Sciascia |

FOREIGN PATENT DOCUMENTS

| | | | |
|---|---|---|---|
| EP | 0615756 A1 | 9/1994 | |
| TW | 399056 B | 7/2000 | |
| TW | 1226239 B | 1/2005 | |
| TW | 201416074 A | 5/2014 | |
| WO | WO-2007061896 A1 * | 5/2007 | .......... A61K 9/0024 |
| WO | WO 2013167735 A1 | 11/2013 | |

OTHER PUBLICATIONS

FDA, Center for Drug Evaluation and Research, Mar. 2014 (Year: 2014).*
Mackey et al., Hum Reprod. Apr. 1995; 10(4):862-5 (Year: 1995).*
Baxter, et al., "A dose-response study of nalbuphine for post-thoracotomy epidural analgesia", *Canadian Journal of Anesthesia* 1991; 38(2):175-182.
Huang, et al., "Simultaneous determination of nalbuphine and its prodrug sebacoly (sic) dinalbuphine ester in human plasma by ultra-performance liquid chromatography-tandem mass spectrometry and its application to pharmacokinetic study in humans", *Biomed. Chromatography* 2013; 27:831-837.

(Continued)

*Primary Examiner* — Jean P Cornet
(74) *Attorney, Agent, or Firm* — Finnegan, Henderson, Farabow, Garrett & Dunner, LLP

(57) ABSTRACT

The present invention relates to injectable, extended-release, pharmaceutical formulations comprising a nalbuphine ester prodrug homogenously dissolved in a solution comprising a pharmaceutically acceptable oil and an oil-miscible retaining solvent, as well as manufacturing processes and medical uses of the formulations. The invention further provides methods for adjusting the duration of action of the formulations by varying the ratio of the pharmaceutically acceptable oil and the oil-miscible retaining solvent.

37 Claims, 8 Drawing Sheets

(56) References Cited

OTHER PUBLICATIONS

International Search Report and Written Opinion of International Application No. PCT/IB2015/001758 dated Feb. 18, 2016 (17 pages).
Kalicharan, et al., "Fundamental understanding of drug absorption from a parenteral oil depot", *European Journal of Pharmaceutical Sciences* 2016; 83:19-27.
Lo, et al., "The pharmacokinetics of intravenous, intramuscular, and subcutaneous nalbuphine in healthy subjects", *European Journal of Clinical Pharmacology* 1987; 33:297-301.
Pao, et al., "High performance liquid chromatographic method for the simultaneous determination of nalbuphine and its prodrug, sebacoyl dinalbuphine ester, in dog plasma and application to pharmacokinetic studies in dogs", *J Chromatogr B Biomed Sci Appl.* 2000; 746:241-247.
Pao, et al., "In vitro and in vivo evaluation of the metabolism and pharmacokinetics of sebacoyl dinalbuphine", *Drug Metabolism and Disposition* 2005; 33(3):395-402.
Patel, "Parenteral suspension: an overview", *International Journal of Current Pharmaceutical Research* 2010; 2(3):4-13.
Savva et al., (2014) "Pharmacotherapy of Persisting Pain in Children and Adolescents When Providing Palliative Care Under Inpatient and Outpatient Conditions", Moscow (23 pages).
Titulaer, et al., "The pharmacokinetics of artemisinin after oral, intramuscular and rectal administration to volunteers", *Journal of Pharmacy and Pharmacology* 1990; 42(11):810-813.
*United States Pharmacopeia and National Formulary* (USP 39-NF 34). vol. 1, Rockville, MD: United States Pharmacopeial Convention: 2016 (excerpt); pp. 68-77 (6 pages).
U.S. Appl. No. 15/166,403, Restriction Requirement dated Dec. 27, 2016, (10 pages).
U.S. Appl. No. 15/166,403, Non-final Office Action dated Nov. 13, 2017, (14 pages).
U.S. Appl. No. 15/166,403, Final Office Action dated Jun. 26, 2018, Jean P Cornet (10 pages).
U.S. Appl. No. 15/166,403, Notice of Allowance dated Sep. 17, 2018, (10 pages).

* cited by examiner dom
PHARMACEUTICAL FORMULATIONS FOR SUSTAINED RELEASE OF SEBACOYL DINALBUPHINE ESTER This application is a continuation of U.S. patent application Ser. No. 16/195,187, filed Nov. 19, 2018, which is a continuation of U.S. patent application Ser. No. 15/166,403, filed May 27, 2016, now U.S. Pat. No. 10,183,018, which is a continuation-in-part of U.S. patent application Ser. No. 14/723,996, filed May 28, 2015, and also claims priority to U.S. Provisional Application No. 62/255,805, filed Nov. 16, 2015. These references are incorporated herein by reference.

FIELD OF THE INVENTION

The present invention generally relates to pharmaceutical compositions. More particularly, the present invention relates to extended release formulations of nalbuphine ester prodrugs such as sebacoyl dinalbuphine ester "SDE").

BACKGROUND OF THE INVENTION

Opioids have been widely regarded as the most effective drugs for the treatment of pain, and the use of opioids in the management of acute severe pain and chronic pain is considered the standard of care Prescription opioids are available as immediate-release (IR) or extended release (ER) formulations. Compared with IR formulations, ER formulations allow a controlled release of the active agent to provide a prolonged plasma drug level within the therapeutic window; ER formulations also provide a lower maximum concentration ($C_{max}$), fewer peak-to-trough fluctuations, and less frequent dosing (J Multidiscip Healthc. 2013; 6: 265-280). However, the effective duration of most of the current market available extended release opioids is less than 3 days. For example, nalbuphine is a short-acting drug with a duration of action of 3-5 hours after being administered via intravenous (IV), subcutaneous (SC), or intramuscular (IM) injection. As such, frequent injections or administrations of nalbuphine are needed for patients suffering from dramatic or long-lasting pain.

U.S. Pat. No. 6,197,344 discloses several controlled release suspension formulations for subcutaneous administration, each of which comprises the opioid analgesic butorphanol in the form of microparticles having an average particle size of from about 5 to 25 microns. It is stated that the suspension formulations can be used to relieve pain for 12 to 24 hours. Furthermore, because the particle sizes of butorphanol microparticles are too large, the suspensions are considered not suitable for being administered by intramuscular injection or for being sterilized by filtration.

U.S. Pat. No. 8,455,508 discloses an oil- and pH-controlled buprenorphine-release formulation, which can be administered by subcutaneous or intramuscular injection. The formulation is in the form of an emulsion and needs to be prepared through several sterilizing procedures during its manufacturing process, which is time-consuming and not cost effective in large scale production.

U.S. Pat. No. 6,225,321 discloses several extended release formulations for intramuscularly administrating nalbuphine ester prodrugs, e.g., sebacoyl dinalbuphine ester ("SDE"). The formulations are prepared by mixing the nalbuphine ester prodrugs with therapeutically injectable oils and excipients (such as methyl paraben, propyl paraben, BHA, BHT, cremophore EL, pluronic, solutol, or span). It is stated that a single dose of the formulation could give an analgesic effect maintained for 4 to 5 days when the injection volume is 7.15 mL. However, 5 mL was reported for adults as the maximum volume for a single intramuscular injection. Large-volume injections (3 mL or greater) are rarely administered clinically, and may cause serious injection site irritation.

U.S. Pat. No. 6,703,398 discloses formulations for orally administrating nalbuphine or nalbuphine ester. The oral formulations are prepared by mixing nalbuphine or nalbuphine ester with an oily substance, and a solubility-assisting agent. It is stated that the solubility-assisting agent is used to improve bioavailability and half-life of nalbuphine or nalbuphine ester. However, the apparent half-life ($t_{1/2}$) of nalbuphine from the oral formulation was only about 24 hours, and it would require the dosing interval of the oral formulation to be approximately every 8 to 12 hours to exert efficacy. Such a dosing frequency is not practical or desirable for patients suffering from long-term or severe pain, for example, post-surgical pain.

Although the use of emulsion or oil-based vehicles in preparing extended release formulations of opioids is not unknown, the complexity of sterilization and the limited solubility of nalbuphine ester prodrugs in oily substances make it difficult to achieve extended release formulations which can release nalbuphine ester prodrugs in a well-controlled manner, can be administered to patients in a low injection volume, and can be prepared by a simple and cost-effective method, applicable in industrial scale manufacturing. There is a need to prepare extended release formulations with predetermined release periods by simple and cost effective methods.

BRIEF SUMMARY OF THE INVENTION

The following presents a simplified summary of the invention in order to provide the reader a basic understanding. This summary is not an extensive overview of the invention. It is not intended to, and does not, delineate the scope of the present invention. Rather, its sole purpose is to present some concepts disclosed herein in a simplified form as a prelude to the more detailed description that is presented later.

In one aspect, the present disclosure provides pharmaceutical formulations each comprising a nalbuphine ester prodrug and a release-controlling solution, wherein the formulations are suitable for administration by injection and release the nalbuphine ester prodrug in an extended manner. In some embodiments, the nalbuphine ester prodrug is homogenously dissolved in the release-controlling solution. In some embodiments, the release-controlling solution comprises an oil-miscible retaining solvent and a pharmaceutically acceptable oil.

The present disclosure also provides pharmaceutical formulations each comprising the nalbuphine ester prodrug dissolved in the pharmaceutically acceptable oil and the oil-miscible retaining solvent. In some embodiments, the concentration of the nalbuphine ester prodrug in the formulation is greater than the solubility of the nalbuphine ester prodrug when added to a mixture of the pharmaceutically acceptable oil and the oil-miscible retaining solvent. In some embodiments, the weight ratio of the oil-miscible retaining solvent to the pharmaceutically acceptable oil is equal to or greater than about 1.1:1. Such pharmaceutical formulations may provide an extended release period of the nalbuphine ester prodrug.

The inventors have discovered that by increasing the weight ratio of the oil-miscible retaining solvent to the pharmaceutically acceptable oil (the "retaining solvent/oil ratio"), the release period of the nalbuphine ester prodrug from the formulation may be extended. In some embodiments, the nalbuphine ester prodrug is sebacoyl dinalbuphine ester (SDE). The pharmaceutically acceptable oil may be a vegetable oil, for example, sesame oil, cottonseed oil, castor oil or a mixture thereof. The oil-miscible retaining solvent may be benzyl benzoate, benzyl alcohol, or a mixture thereof. In some embodiments, the pharmaceutically acceptable oil is sesame oil and the oil-miscible retaining solvent is benzyl benzoate.

In some embodiments, the solubility of the prodrug, e.g., SDE, in the oil-miscible retaining solvent is equal to or greater than about 100 mg/mL. For example, the solubility of SDE in the oil-miscible retaining solvent may be equal to or greater than 300 mg/mL.

In some embodiments, the concentration of the prodrug, e.g., SDE, in the formulation is equal to or greater than about 70 mg/mL. For example, the concentration of SDE in the formulation may be about 70-300 mg/mL, 70-150 mg/mL, or about 70-100 mg/mL. In some embodiments, the concentration of SDE in the formulation is about 75 mg/mL or about 80 mg/mL.

In some embodiments, the retaining solvent/oil ratio is about 0.5 to about 19. In some embodiments, the retaining solvent/oil ratio is equal to or greater than 1.1:1. For example, the retaining solvent/oil ratio may be about 0.8-1.2:1, about 0.65-2:1, about 1-2:1, or about 1-3:1. In some embodiments, the retaining solvent/oil ratio is about 1.12:1, about 1.18:1, about 0.65:1, about 2:1 or about 3:1.

In some embodiments, the concentration of SDE in the formulation is about 70-80 mg/mL, and the weight ratio of benzyl benzoate to sesame oil is about 1.1-1.2:1. In one embodiment, the concentration of SDE in the formulation is about 75 mg/mL, and the weight ratio of benzyl benzoate to sesame oil is about 1.12:1. In one embodiment, the concentration of SDE in the formulation is about 80 mg/mL, and the weight ratio of benzyl benzoate to sesame oil is about 1.18:1.

In some embodiments, the concentration of the nalbuphine ester prodrug in the formulation is greater than the solubility of the nalbuphine ester prodrug when added to the mixture of the pharmaceutically acceptable oil and the oil-miscible retaining solvent. For example, the nalbuphine ester prodrug may be SDE; the pharmaceutically acceptable oil may be sesame oil and the oil-miscible retaining solvent may be benzyl benzoate; the weight ratio of benzyl benzoate to sesame oil may be about 0.8-1.2:1; and the concentration of SDE in the formulation may be greater than about 70 mg/mL.

In some embodiments, the weight ratio of the oil-miscible retaining solvent to the pharmaceutically acceptable oil is equal to or greater than about 1.1:1. For example, the nalbuphine ester prodrug may be SDE; the pharmaceutically acceptable oil may be sesame oil and the oil-miscible retaining solvent may be benzyl benzoate; the weight ratio of benzyl benzoate to sesame oil may be about 1.1-3:1; and the concentration of SDE in the formulation may be greater than about 70 mg/mL.

In some embodiments, the formulation is an extended or sustained release formulation. In some embodiments, the present formulation has a duration of action of equal to or greater than about 5 days, or about 6 days. In some embodiments, the present formulation has a release period of equal to or greater than about 10 days, about 12 days, or about 14 days. In some embodiments, the retaining solvent/oil ratio is greater than about 1, and the duration of action of the pharmaceutical formulation is equal to or greater than about 5 days or about 6 days, and/or the release period of the pharmaceutical formulation is equal to or greater than about 10 days, about 12 days or about 14 days. In some embodiments, the retaining solvent/oil ratio is less than about 1, and the duration of action of the pharmaceutical formulation is less than about 6 days, and/or the release period of the pharmaceutical formulation is less than about 14 days.

The present formulations may be intramuscularly or subcutaneously administered to a subject. In some embodiments, the present formulation is suitable for administration by intramuscular injection.

In some embodiments, the formulation further comprises adding a solubilizing agent and/or a neutralizing agent.

In another aspect, the present invention provides a method for preparing an extended release formulation comprising a nalbuphine ester prodrug with a predetermined release period, comprising providing an oil-miscible retaining solvent and a pharmaceutically acceptable oil, wherein the weight ratio of the retaining solvent to the oil is adjusted based on the predetermined release period; and mixing the nalbuphine ester prodrug with the retaining solvent and the oil to give a homogeneously dissolved solution. In some embodiments, the step of mixing the prodrug with the retaining solvent and the oil comprises mixing the prodrug with the oil-miscible retaining solvent to give a clear solution, and then mixing the clear solution with the pharmaceutically acceptable oil. In some embodiments, the step of mixing the prodrug with the retaining solvent and the oil comprises mixing the prodrug with a mixture of the oil-miscible retaining solvent and the pharmaceutically acceptable oil.

In some embodiments, the predetermined release period is equal to or greater than about 10 days, about 12 days or about 14 days, and the retaining solvent/oil ratio is adjusted to greater than about 1. For example, when a duration of action of equal to or greater than about 5 or 6 days is intended for the present formulation, the retaining solvent/oil ratio may be adjusted to greater than about 1. When a duration of action of equal to or greater than about 5 or 6 days, and/or a release period of equal to or greater than 14 days, is intended for the present formulation, the retaining solvent/oil ratio may be adjusted to greater than about 1. In some embodiments, the predetermined release period is less than about 14 days, and the retaining solvent/oil ratio can be adjusted to less than about 1. In some embodiments, when a duration of action of less than about 6 days, and/or a release period of less than 14 days, is intended for the present formulation, the retaining solvent/oil ratio can be adjusted to less than about 1.

The present invention also provides a method for preparing a pharmaceutical formulation, comprising dissolving the nalbuphine ester prodrug in the oil-miscible retaining solvent; and mixing the resulting solution with the pharmaceutically acceptable oil to give a homogenous solution, wherein the formulation is suitable for administration by injection. In some embodiments, the nalbuphine ester prodrug is dissolved in the formulation at a concentration greater than the solubility of the nalbuphine ester prodrug when added to a mixture of the oil-miscible retaining solvent and the pharmaceutically acceptable oil.

In some embodiments, the nalbuphine ester prodrug is SDE. In some embodiments, the solubility of the prodrug, e.g., SDE, in the oil-miscible retaining solvent is equal to or greater than about 100 mg/mL. In some embodiments, the concentration of the prodrug, e.g., SDE, in the formulation is greater than about 70 mg/mL. In some embodiments, the pharmaceutically acceptable oil is soybean oil, peanut oil, sesame oil, or a mixture thereof; and the oil-miscible retaining solvent is benzyl benzoate, benzyl alcohol, or a mixture thereof. For example, the oil may be sesame oil and the retaining solvent may be benzyl benzoate. In some embodiments, the weight ratio of benzyl benzoate to sesame oil is about 0.8-1.2:1. In some embodiments, the formulation is suitable for administration by intramuscular or subcutaneous injection.

In some embodiments, the method can further comprise adding a solubilizing agent and/or a neutralizing agent.

In some embodiments, the methods of the invention can further include the step of filtering the resulting homogeneous solution with a bacteria proof filter.

In another aspect, the present invention provides a method of treating pain, comprise administering a therapeutically effective amount of the pharmaceutical formulation of the invention to a subject in need thereof. In some embodiments, the formulation being administered substantially consists of SDE, sesame oil and benzyl benzoate, wherein the weight ratio of benzyl benzoate to sesame oil is about 0.8-1.2:1. In some embodiments, the concentration of SDE in the formulation being administered is greater than about 70 mg/mL.

In some embodiments, the formulation is administered by intramuscular injection. In some embodiments, the formulation is administered 6-36 hours prior to the onset of pain symptoms. In some embodiments, the onset of pain symptoms is during or after a surgical operation on the subject. In some embodiments, the formulation is administered to deliver a total dose of up to about 160 mg of SDE.

It is to be understood that the foregoing general description and the following detailed description are exemplary and explanatory only, and are intended to provide further, non-limiting explanation of the disclosure.

DETAILED DESCRIPTION OF THE INVENTION

Figure 1A:
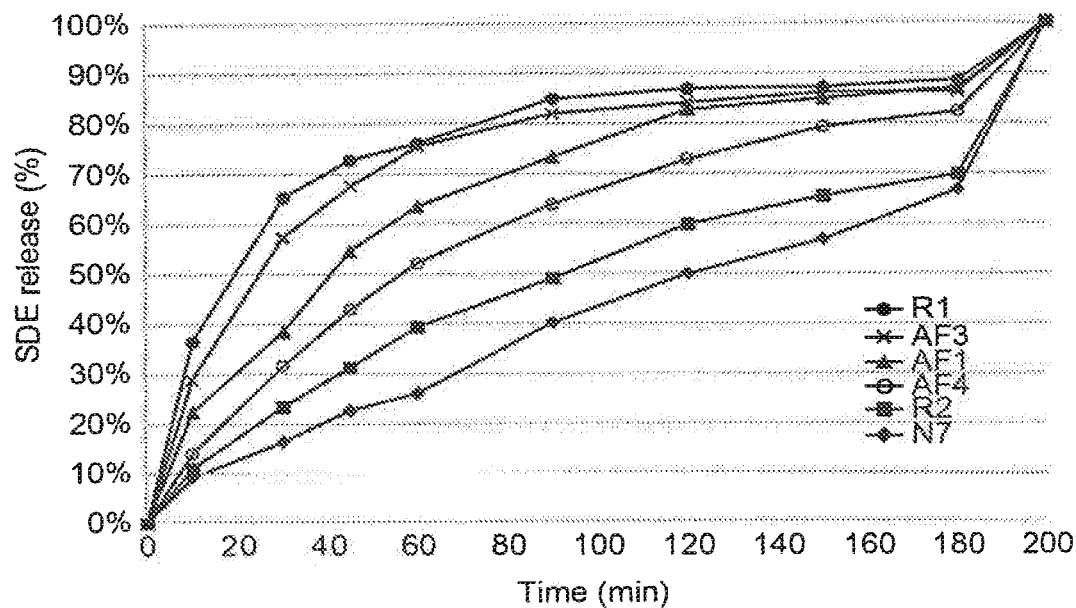
FIG. 1A shows the accumulated dissolution profiles of R1, AF3, AF1, AF4, R2, and N7 formulations.

The following detailed description and examples illustrate certain embodiments of the present invention. Those of skill in the art will recognize that there are numerous variations and modifications of this disclosure that are encompassed by its scope. Accordingly, the description of certain embodiments should not be deemed as limiting.

As used herein, the term "extended release" or a similar expression, for example, "sustained release" means that an active pharmaceutical ingredient or prodrug thereof may be continuously released from a drug formulation or pharmaceutical formulation over an extended period of time after being administered (e.g., 24 hours or longer, such as equal to or greater than 3 days, equal to or greater than 5 days, equal to or greater than 6 days, equal to or greater than 7 days, or equal to or greater than 14 days from dosing). Other related terms include "released in a sustained manner."

As used herein, the term "release period" means a period of time during which an active ingredient or prodrug thereof is available for absorption and pharmacological effect (e.g., to treat pain) after administration.

As used herein, the term "duration of action" means the length of time an active ingredient or prodrug thereof exhibits a desired pharmacologic effect, e.g., an analgesic effect, after administration. This is determined by the amount of time drug concentration is at or above a minimum effective concentration.

As used herein, the term "pharmaceutically acceptable oil" refers to an oil that may be used to prepare pharmaceutical formulations containing an active ingredient, without the oil causing an unacceptable adverse effect. As used herein, the term "therapeutically injectable oil" refers to an oil that can be used to prepare pharmaceutical formulations containing an active ingredient, and the formulations later can be injected into a patient for clinical or therapeutic use, without the oil causing an unacceptable adverse effect. Thus, a "pharmaceutically acceptable oil" may also refer to a "therapeutically injectable oil."

As used herein, the term "release-controlling solution" refers to a solution that may be used to regulate or control the release rate or release period of an active ingredient or prodrug thereof from a formulation.

As used herein, the term "oil-miscible retaining solvent" refers to an organic solvent that is miscible with oil and may be used to slow the release of an active ingredient or prodrug thereof in a formulation so as to modify the rate of drug delivery or to modify the solubility of the drug in the pharmaceutically acceptable oil. Dissolving the drug or pro-drug thereof in the oil-miscible retaining solvent before the pharmaceutically acceptable oil is added may allow for a concentration of drug or prodrug thereof in the formulation that is higher than the solubility of the drug or prodrug when it is added to a pre-made mixture of the oil and the retaining solvent.

As used herein, the term "solubilizing agent" means a substance that may be used to increase the solubility of an active ingredient or prodrug thereof in a liquid formulation, and is miscible with the liquid formulation.

As used herein, the term "neutralizing agent" means a substance that may be used to neutralize an acid generated during or after administration of a drug formulation.

As used herein, the word "dissolve" (e.g., as in fully dissolve) or "dissolved" means that a non-aqueous substance (e.g., a solid) becomes or causes to become incorporated into a liquid so as to form a homogeneous solution.

As used herein, the term "homogenously dissolved" means that a non-liquid (e.g., a solid or amorphous) compound is completely dissolved in a solvent, or a solvent system or mixture, to give a homogenous solution which, for example, does not contain particles or precipitates of the compound to be dissolved.

As used herein, the terms "suitable for injection" or "suitable for administration by injection" mean that a pharmaceutical composition is in such a form or state that makes it clinically possible or ideal for administration by injection, e.g., subcutaneous injection, intravenous injection, or intramuscular injection.

As used herein, the term "solubility" means the maximum amount of a solute (e.g., an active ingredient or a prodrug thereof) that can be dissolved in a given amount of a solvent at a particular temperature. Unless otherwise specified, the solubilities presented herein are at room temperature (e.g., 25-28° C.). The term "saturated concentration" refers to the concentration at which no more of a solute will dissolve in a solvent and additional amounts of solute will appear as a separate phase (e.g., as a precipitate).

As used herein, the singular forms "a", "and", and "the" are used herein to include plural referents unless the context clearly dictates otherwise.

As used herein, the term "about" means within an acceptable standard error of the mean when considered by one of ordinary skill in the art. Other than in the operating/working examples, or unless otherwise expressly specified, all of the numerical ranges, amounts, values, and percentages such as those for quantities of materials, durations of times, temperatures, operating conditions, ratios of amounts, or reflection angles disclosed herein should be understood as modified in all instances by the term "about." In the context of the retaining solvent/oil ratio, of the concentration of nalbuphine ester prodrug, or of time, for example, the amount of time for each step of the disclosed methods, "about" as used herein indicates that the calculation or the measurement of the value allows some slight imprecision without having a substantial effect on the chemical or physical attributes of the disclosed formulations or methods. If, for some reason, the imprecision provided by "about" is not otherwise understood in the art with this ordinary meaning, then "about" as used herein indicates a possible variation of up to 5% in the value.

Unless defined otherwise, all technical and scientific terms used herein have the same meaning as commonly understood by one of the ordinary skill in the art to which this invention belongs.

Pharmaceutical Formulations

In one aspect, the present invention provides pharmaceutical formulations each comprising a nalbuphine ester prodrug and a release-controlling solution, wherein the formulations are suitable for administration by injection and release the nalbuphine ester prodrug in an extended or sustained manner. In some embodiments, the nalbuphine ester prodrug is homogenously dissolved in the release-controlling solution. The release-controlling solution may comprise an oil-miscible retaining solvent and a pharmaceutically acceptable oil.

The present disclosure also provides pharmaceutical formulations each comprising the nalbuphine ester prodrug dissolved in the pharmaceutically acceptable oil and the oil-miscible retaining solvent. In some embodiments, the concentration of the nalbuphine ester prodrug in the formulation is greater than the solubility of the nalbuphine ester prodrug when added to a mixture of the pharmaceutically acceptable oil and the oil-miscible retaining solvent. In some embodiments, the weight ratio of the oil-miscible retaining solvent to the pharmaceutically acceptable oil is equal to or greater than about 1.1:1. Such pharmaceutical formulations may provide an extended release period of the nalbuphine ester prodrug.

The nalbuphine ester prodrug may show a better solubility in an oily substance as compared with nalbuphine. For example, the prodrug may be any of the nalbuphine polyester derivatives disclosed in U.S. Pat. No. 6,225,321. In some embodiments, the nalbuphine ester prodrug may be sebacoyl dinalbuphine ester ("SDE"). In some embodiments, the concentration of SDE in the formulation is about 70-300 mg/mL, about 70-150 mg/mL, or about 70-100 mg/mL. For example, the concentration of SDE in the formulation may be about 70 mg/mL, about 75 mg/mL, about 80 mg/mL, about 100 mg/mL, or about 150 mg/mL.

In some embodiments, the solubility of the nalbuphine ester prodrug in the retaining solvent is equal to or greater than about 100 mg/mL. In other embodiments, the oil-miscible retaining solvent can dissolve the nalbuphine ester prodrug at a high concentration, e.g., more than about 150 mg/mL, or more than about 300 mg/mL, and is miscible with the pharmaceutically acceptable oil. In some embodiments, the oil-miscible retaining solvent is benzyl benzoate, benzyl alcohol, or any mixture thereof, and the nalbuphine ester prodrug is SDE. The solubilities of SDE in benzyl benzoate and benzyl alcohol are greater than 300 mg/mL and greater than 500 mg/mL, respectively.

The pharmaceutically acceptable oil may be a vegetable oil. In some embodiments, the pharmaceutically acceptable oil may be sesame oil, castor oil, cottonseed oil, soybean oil, corn oil, sunflower oil, arachis oil, olive oil, or any mixture thereof. In some embodiments, the oil is sesame oil, cottonseed oil, or castor oil. For example, the oil may be sesame oil.

The oil-miscible retaining solvent may be an organic solvent that is miscible with the pharmaceutically acceptable oil, for example, benzyl benzoate, benzyl alcohol, or a mixture thereof. In some embodiments, the retaining solvent is benzyl benzoate. For example, the pharmaceutically acceptable oil may be sesame oil and the oil-miscible retaining solvent may be benzyl benzoate.

The pharmaceutically acceptable oil is miscible with the retaining solvent. When the formulation is administered into a subject by subcutaneous or intramuscular injection, the oil and the retaining solvent may form a matrix to retain the nalbuphine ester prodrug, so as to release the prodrug from the formulation in an extended/controlled manner. When the weight ratio of the retaining solvent to the oil is increased, the release period of the prodrug from the formulation may be extended or prolonged. Without wishing to limit the invention to any particular theory or mechanism of operation, it is believed that the oil-miscible retaining solvent serves as the key element in the formulation to retain the prodrug in the matrix.

As used herein, retaining solvent/oil ratios may be expressed as either, for example, 3:1 or 3. For example, a retaining solvent/oil ratio expressed as 0.5:1 is the same as a retaining solvent/oil ratio expressed as 0.5. A range of retaining solvent/oil ratios may be expressed as 1:1-3:1, 1-3:1 or 1-3, for example.

By controlling/adjusting the retaining solvent/oil ratio, the present formulations may regulate the release rate/release period of the nalbuphine ester prodrug from the formulation. For example, when the retaining solvent/oil ratio is adjusted to 3:1, the formulation may show a release period significantly longer than that of the formulation with a retaining solvent/oil ratio of 0.5:1. In some embodiments, when the retaining solvent/oil ratio is adjusted to about 0.65, about 99% of the prodrug is released from the formulation at 144 hours from dosing; when the retaining solvent/oil ratio is adjusted to about 1, about 90% of the prodrug is released from the formulation at 144 hours from dosing; when the retaining solvent/oil ratio is adjusted to about 2, about 80% of the prodrug is released from the formulation at 144 hours from dosing. In some embodiments, when the retaining solvent/oil ratio is adjusted to greater than about 1, the present formulation may have a release period of equal to or greater than 10 days, 12 days or 14 days. In some embodiments, when the retaining solvent/oil ratio is adjusted to greater than about 1, the present formulation may have a duration of action of equal to or greater than 5 days or 6 days.

In some embodiments, when the retaining solvent/oil ratio is adjusted to greater than about 1, the present formulation may have a release period of equal to or greater than 14 days or may have a duration of action of equal to or greater than 6 days. In some embodiments, when the retaining solvent/oil ratio is adjusted to about 1-3 or about 1-2, the present formulation may have a duration of action of equal to or greater than about 5 or 6 days, and/or a release period of equal to or greater than about 10, 12 or 14 days. In some embodiments, when the retaining solvent/oil ratio is adjusted to less than about 1, the present formulation may have a release period of less than 14 days, and/or a duration of action of less than 6 days.

In some embodiments, the retaining solvent/oil ratio is about 0.5 to about 19. In some embodiments, the retaining solvent/oil ratio is about 0.65-8:1, about 0.65-3:1, about 0.65-2:1, about 1-8:1, about 1-3:1, about 1-2:1, or about 0.8-1.2:1. For example, the retaining solvent/oil ratio may be about 0.5, 0.65, 0.8, 1, 1.12, 1.18, 1.2, 2, 3 or 8.

In some embodiments, the oil-miscible retaining solvent is benzyl benzoate, benzyl alcohol, or any mixture thereof; the nalbuphine ester prodrug is SDE; and the pharmaceutically acceptable oil is sesame oil, cottonseed oil, castor oil, or any mixture thereof. For example, the oil-miscible retaining solvent may be benzyl benzoate, the nalbuphine ester prodrug may be SDE, and the oil may be sesame oil, where the weight ratio of benzyl benzoate to the oil (the "BB/oil ratio") may be about 0.5 to about 16. The present formulations when being prepared with the BB/oil ratio of 16 may show a longer release period than as prepared with the BB/oil ratio of 0.5. In some embodiments, the BB/oil ratio is about 0.65-8:1, about 0.65-3:1, about 0.65-2:1, about 1-8:1, about 1-3:1, about 1-2:1, or about 0.8-1.2:1. For example, the BB/oil ratio may be about 0.5, 0.65, 0.8, 1, 1.12, 1.18, 1.2, 2, 3 or 8. In embodiments where the BB/oil ratio is adjusted to about 1:12, the present formulation may have a release period of equal to or greater than about 10 days, 12 days or 14 days, and/or a duration of action of equal to or greater than about 5 days or 6 days. In particular, when BB/oil ratio is adjusted to about 1:12, the present formulation may have a release period of equal to or greater than about 14 days, and/or have a duration of action of equal to or greater than about 6 days.

In some embodiments, the oil-miscible retaining solvent is a mixture of benzyl benzoate and benzyl alcohol. In some embodiments, the combined weight ratio of benzyl benzoate and benzyl alcohol to the pharmaceutically acceptable oil ("BB+BA/oil ratio") may be 0.5-19, about 0.82-19, about 0.5-16, about 0.65-8:1, about 0.65-3:1, about 1-8:1, or about 1-3:1. In some embodiments, the BB+BA/oil ratio may be about 0.82:1 or about 19:1.

In some embodiments, the present formulation comprises SDE, benzyl benzoate, and sesame oil, wherein the formulation is administered to a subject by intramuscular injection, the weight ratio of benzyl benzoate to sesame oil is greater than 1:1, the concentration of SDE in the formulation is greater than 70 mg/mL, and the duration of action of the formulation is equal to or greater than 6 days.

In some embodiments, the pharmaceutical formulations of the present invention are suitable for injection into a subject in need thereof. It is known in the art that a formulation has to be a homogeneous solution or a homogeneous suspension in order to be qualified as an injectable formulation. More particularly, an injectable suspension should contain at most 0.5-5.0% solids and have an average particle size of less than 5 micrometers in order to be used as a pharmaceutically acceptable suspension for intramuscular injection (see R. M. Patel, Parenteral Suspension: an Overview, *Int. J. Curr. Pharm. Res.*, 2010, 2(3):3-13). In some embodiments, the formulations of the present disclosure are homogeneous and stable solutions and, therefore, are suitable for administration by intramuscular injection. In some embodiments, the nalbuphine ester prodrug is homogenously dissolved in the formulation.

It should be understood that, due to the difference between the solubility of SDE in the retaining solvent and in the oil, the solubility of SDE is higher in formulations with higher retaining solvent/oil ratios. For example, the solubilities of SDE in benzyl benzoate and benzyl alcohol are greater than 300 mg/mL and greater than 500 mg/mL, respectively, while the solubilities of SDE in sesame oil, castor oil, and cottonseed oil are about 6 mg/mL, about 13 mg/mL, and about 6 mg/mL, respectively. Based on a series of solubility tests conducted by the inventors, it was demonstrated that when the weight ratio of benzyl benzoate to sesame oil is about 1, the solubility (i.e., the saturated concentration) of SDE when added to the mixture of benzyl benzoate and sesame oil is about 60-65 mg/mL; when the weight ratio of benzyl benzoate to sesame oil is about 1.1, the solubility of SDE when added to the mixture of benzyl benzoate and sesame oil is about 70 mg/mL; when the weight ratio of benzyl benzoate to sesame oil is about 1.5, the solubility of SDE when added to the mixture of benzyl benzoate and sesame oil is about 150 mg/mL; when the weight ratio of benzyl benzoate to sesame oil is about 2.3, the solubility of SDE when added to the mixture of benzyl benzoate and sesame oil is about 200 mg/mL; when the weight ratio of benzyl benzoate to sesame oil is about 9, the solubility of SDE when added to the mixture of benzyl benzoate and sesame oil is greater than 300 mg/mL.

In some embodiments, the concentration of the nalbuphine ester prodrug in the formulation is greater than the solubility of the nalbuphine ester prodrug when added to the mixture of the pharmaceutically acceptable oil and the oil-miscible retaining solvent. For example, the prodrug may be SDE, the retaining solvent may be benzyl benzoate, the oil may be sesame oil, and the retaining solvent/oil ratio, e.g., the BB/oil ratio, may be set to about 1 or about 0.8-1.2:1, so as to give a predetermined release period or a desired duration of action. In this case, the concentration of SDE in the formulation may be increased from about 60-65 mg/mL (the solubility of SDE in the mixture of benzyl benzoate and sesame oil with the BB/oil ratio of about 1) to about 70-100 mg/mL by using the following manufacturing process: a) fully dissolving SDE in benzyl benzoate, and b) mixing the resulting solution with sesame oil to give a homogenous solution. In this preparative method of the present invention, SDE is first dissolved in benzyl benzoate to form a clear solution which is then mixed with sesame oil to give a homogeneous solution, by which a homogenous and stable formulation having a BB/oil ratio of about 0.8-1.2:1 and a high concentration of SDE (such as 70-100 mg/mL) can be prepared. The formulations prepared accordingly are stable and have a long shelf-life, staying homogenous and free from forming solid particles or precipitates even after being stored at 2-8° C. for at least 24 months. Therefore, the formulations are suitable for administration by intramuscular injection.

In some embodiments, the retaining solvent/oil ratio is equal to or greater than about 1.1:1. For example, the prodrug may be SDE, the retaining solvent may be benzyl benzoate, the oil may be sesame oil, and the retaining solvent/oil ratio, e.g., the BB/oil ratio, may be set to about 1.1, so as to give a predetermined release period or a desired duration of action. In some embodiments, the concentration of the nalbuphine ester prodrug in the formulation is greater than the solubility of the nalbuphine ester prodrug when added to the mixture of the pharmaceutically acceptable oil and the oil-miscible retaining solvent and the retaining solvent/oil ratio is equal to or greater than about 1.1:1.

In one embodiment, the nalbuphine ester prodrug is SDE; the pharmaceutically acceptable oil is sesame oil; the oil-miscible retaining solvent is benzyl benzoate; the weight ratio of benzyl benzoate to sesame oil is about 1.1-3:1; and the concentration of SDE in the formulation is greater than about 70 mg/mL.

In some embodiments, the retaining solvent/oil ratio is equal to or greater than about 1.5:1. In some embodiments, the concentration of the nalbuphine ester prodrug in the formulation is greater than the solubility of the nalbuphine ester prodrug when added to the mixture of the pharmaceutically acceptable oil and the oil-miscible retaining solvent and the retaining solvent/oil ratio is equal to or greater than about 1.5:1. In one embodiment, the nalbuphine ester prodrug is SDE, the pharmaceutically acceptable oil is sesame oil, and the oil-miscible retaining solvent is benzyl benzoate.

It should be understood that when the BB/oil is increased, for example, from about 1 to about 1.5, the solubility of SDE in the formulation will be increased significantly, for example, from about 60 mg/mL to about 150 mg/mL. When the formulation is intended to be prepared with a SDE concentration greater than the solubility of SDE when added to the mixture of benzyl benzoate and sesame oil, the homogeneously dissolved solution can only be prepared by mixing SDE with benzyl benzoate to form a clear solution, and then mixing the clear solution with sesame oil. When the formulation is intended to be prepared with a SDE concentration equal to or lower than the solubility of SDE when added to the mixture of benzyl benzoate and sesame oil, the homogeneously dissolved solution may be given either by mixing SDE directly with the mixture of benzyl benzoate and sesame oil, or by pre-dissolving SDE with benzyl benzoate.

In some embodiments, the BB/oil ratio is equal to or greater than about 1.1:1, and the concentration of SDE in the formulation is greater than about 70 mg/mL. For example, the BB/oil ratio may be about 1.1:1, and the concentration of SDE in the formulation may be about 70-100 mg/mL.

In some embodiments, the nalbuphine ester prodrug is SDE; the pharmaceutically acceptable oil is sesame oil and the oil-miscible retaining solvent is benzyl benzoate; the weight ratio of benzyl benzoate to sesame oil is about 0.8-1.2:1; and the concentration of SDE in the formulation is greater than about 70 mg/mL.

In some embodiments, the concentration of SDE in the formulation is about 70-80 mg/mL, and the weight ratio of benzyl benzoate to sesame oil is about 1.1-1.2:1. In one embodiment, the concentration of SDE in the formulation is about 75 mg/mL, and the weight ratio of benzyl benzoate to sesame oil is about 1.12:1. In one embodiment, the concentration of SDE in the formulation is about 80 mg/mL, and the weight ratio of benzyl benzoate to sesame oil is about 1.18:1.

In some embodiments, the formulations can further comprise a solubilizing agent. The solubilizing agent may help to increase the concentration of the nalbuphine ester prodrug in the formulation; in the meantime, the solubilizing agent is miscible with the release-controlling solution. For example, the solubilizing agent may be an alkyl alcohol. When the alkyl alcohol is used independently to dissolve the nalbuphine ester prodrug, the solubility of the prodrug in the alkyl alcohol may be relatively low. For example, the solubilities of SDE in ethanol, 1-propanol and t-butanol are about 16 mg/mL, about 32 mg/mL, and about 19 mg/mL, respectively. However, in some embodiments, when the alkyl alcohol is added into the present formulations, the solubility of the prodrug in the formulations may be increased by at least 30%. For example, the solubility of SDE in the formulations may be increased from about 160 mg/mL to about 210 mg/mL when 10% by weight of tert-Butanol is used to replace the corresponding amount of benzyl benzoate in the formulations.

The solubilizing agent may be a C2-C6 alkyl alcohol or any mixture thereof. The C2-C6 alkyl alcohol may be a linear or branched alkyl alcohol. In some embodiments, the alkyl alcohol may be a C2-C5 alkyl alcohol, such as ethanol, 1-propanol, isopropanol, 1-butanol, sec-butanol, isobutanol, tert-butanol, n-pentanol, 2-pentanol, 3-pentanol, 2-methyl-1-butanol, 2-methyl-2-butanol, 3-methyl-2-butanol, 3-methyl-1-butanol, and/or 2,2-dimethyl-1-propanol. In some embodiments, the alkyl alcohol may be ethanol, 1-propanol, 2-propanol, 1-butanol, and/or tert-butanol. In some embodiments, the w/w % of the alkyl alcohol in the solvent system (i.e., the sum of the alkyl alcohol, the retaining solvent and the oil) is about 2.5-30%, for example, 2.5%, 5%, 10%, 15%, 20% or 30%. In some embodiments, the w/w % of the alkyl alcohol in the solvent system is about 10-20%. In some embodiments, the solubilizing agent may be used to increase the solubility of nalbuphine ester prodrug in the final formulations to more than 100 mg/mL, for example, more than 150, 200, 250, or 300 mg/mL. In some embodiments, the solubilizing agent may be used to increase the concentration of nalbuphine ester prodrug in the final formulations by at least 30%.

It should be understood that the preparation of an oil-containing formulation with a high concentration of SDE is challenging due to the low solubility of SDE in the oil. Clinically, 5 mL has been cited for human adults as the maximum volume for a single IM injection. When preparing an injectable extended release formulation of SDE, the longer the effective release period is expected to be, the higher the drug load should be. In the situation that the injection volume is limited to less than 5 mL (even lower for adults with less muscle mass), the concentration of SDE must be increased in order to increase the drug load. The pre-dissolving of SDE in the retaining solvent and the addition of the solubilizing agent, particularly ethanol, may, respectively, significantly increase the solubility of SDE in the formulation, by which a long-term release formulation of SDE with a high drug-loading can be achieved.

In some embodiments, the pharmaceutical formulations of the present invention each comprise SDE, the release-controlling solution, and the solubilizing agent. In some examples, the release-controlling solution comprises the pharmaceutically acceptable oil selected from the group consisting of sesame oil, castor oil, and cottonseed oil; and the oil-miscible retaining solvent containing benzyl benzoate or benzyl alcohol. In some examples, the solubilizing agent is an alkyl alcohol selected from the group consisting of ethanol, 1-propanol, 2-propanol, 1-butanol, and tert-butanol. In some examples, the w/w % of the pharmaceutically acceptable oil in the solvent system (i.e., the sum of the oil, the retaining solvent, and the solubilizing agent) is about 5%, 10%, 20%, 30%, 40%, 45%, 50%, 55%, or 60%. In some examples, the w/w % of the retaining solvent in the solvent system is about 30%, 35%, 37.5%, 40%, 45%, 47.5%, 50%, 55%, 57.5%, 60%, 65%, 67.5%, 70%, 75%, 77.5%, 80%, or 85%. In some examples, the w/w % of the solubilizing agent in the solvent system is about 2.5%, 5%, 10%, 15%, 20%, or 30%. In some examples, the concentration of SDE in the formulation is above 100 mg/mL, and the solvent system comprises about 2.5-30 w/w % of the alkyl alcohol. In some examples, the concentration of SDE in the formulation is above 150 mg/mL, and the solvent system comprises about 5-30% of the alkyl alcohol. In some examples, the concentration of SDE in the formulation is above 200 mg/mL, and the solvent system comprises about 10-20% of the alkyl alcohol. The formulation may be administered into animals or humans by subcutaneous or intramuscular injection.

The addition of the alkyl alcohol enables the present formulations to be prepared at a higher SDE concentration while showing excellent stability. In some embodiments, the present pharmaceutical formulations are free from forming solid particles or precipitates after being stored at 2-8° C. for at least 24 hours. Moreover, the addition of the alcohol may help to decrease the viscosity of the present formulations, so as to allow an easier injection through a small gauge needle.

In some embodiments, the formulations may further comprise a neutralizing agent, with or without a solubilizing agent. The neutralizing agent may help in neutralizing the acid generated during the conversion of nalbuphine ester prodrug to nalbuphine. For example, when SDE is converted into nalbuphine, sebacoyl acid will be generated. Accumulation of sebacoyl acid may cause injection site irritation. The addition of a neutralizing agent may help to neutralize sebacoyl acid so as to ease the local irritation at the injection site. The neutralizing agent may be a pharmaceutically acceptable basic salt. For example, the basic salt may be a citrate salt, phosphate salt, carbonate salt, lactate salt, tartrate salt, or succinate salt. In some embodiments, the basic salt may be a sodium salt or a potassium salt. In some embodiments, the basic salt may be trisodium citrate, disodium phosphate, sodium bicarbonate, or sodium lactate.

In some embodiments, the pharmaceutical formulations of the present invention each comprise SDE, the release-controlling solution, the solubilizing agent, and the neutralizing agent.

The present pharmaceutical formulations may further comprise suitable inactive ingredients, pharmaceutically or veterinary acceptable carriers, including but not limited to viscosity modifiers, coloring, and flavoring agents, etc.

Methods of Preparation

In some embodiments, the pharmaceutical formulations of the present invention may be prepared without heating steps or complicated mixing sequences.

The present invention also provides methods of preparing an extended release formulation of nalbuphine ester prodrug with a predetermined release period, each comprising:

1) providing an oil-miscible retaining solvent and a pharmaceutically acceptable oil, wherein the weight ratio of the oil-miscible retaining solvent to the pharmaceutically acceptable oil (the "retaining solvent/oil ratio") is adjusted based on the predetermined release period; and 2) mixing the nalbuphine ester prodrug with the oil-miscible retaining solvent and the pharmaceutically acceptable oil, to form a homogeneously dissolved solution.

In some embodiments, the step of mixing the prodrug with the retaining solvent and the oil comprises mixing the prodrug with a mixture of the oil-miscible retaining solvent and the pharmaceutically acceptable oil. For example, when the predetermined release period is set to greater than 14 days, the retaining solvent/oil ratio may be adjusted to greater than 1. For example, the retaining solvent/oil ratio may be about 2. In one embodiment, a release-controlling solution, i.e. the mixture of the retaining solvent and the oil, comprising about 12 g of the retaining solvent and about 6 g of the oil may be firstly prepared and then mixed with about 1.6 g of the prodrug.

In some embodiments, the step of mixing the prodrug with the retaining solvent and the oil comprises the steps of (a) dissolving the nalbuphine ester prodrug in the oil-miscible retaining solvent thereby giving a nalbuphine ester prodrug solution (a clear solution), and (b) mixing the therapeutically acceptable oil with the nalbuphine ester prodrug solution resulting from step (a) to give a homogenously dissolved solution. In some embodiments, the predetermined release period is set to lower than 14 days, the retaining solvent/oil ratio may be adjusted to lower than 1. For example, the retaining solvent/oil ratio may be about 0.65. In one embodiment, about 1.5 g of the prodrug may be dissolved in about 11 g of the retaining solvent to give the clear solution, and the clear solution is then mixed with about 17 g of the oil. In some embodiments, the concentration of the prodrug in the formulation is higher than the solubility of the prodrug when added to the mixture of the retaining solvent and the oil. For example, when the BB/oil ratio is about 1.1, the SDE concentration in the formulation may be about 75 mg/mL or about 80 mg/mL (the solubility of SDE when added into the mixture of benzyl benzoate and sesame oil with a BB/oil ratio of about 1.1 is about 70 mg/mL).

As described above, the nalbuphine ester prodrug is more soluble in formulations with increased retaining solvent/oil ratios, and the duration of drug release is longer for such formulations. When a longer release period is desired, the retaining solvent/oil ratio may be adjusted to a higher value, where the solubility of the prodrug when added to the mixture of the retaining solvent and the oil may be higher than the concentration of the prodrug in the final formulation; accordingly, such a formulation may be prepared either by directly mixing the prodrug with the release-controlling solution (i.e. the mixture of the retaining solvent and the oil), or by pre-dissolving the prodrug in the retaining solvent. However, when a shorter release period in expected, i.e., the retaining solvent/oil ratio is lower, or the intended concentration of the prodrug in the final formulation is equal to or greater than the saturated concentration (i.e. the solubility of the prodrug when added to the mixture of the retaining solvent and the oil), the formulation can be prepared by pre-dissolving the prodrug in the retaining solvent, so that the solubility of the prodrug in the formulation may be significantly improved. As such, the concentration of the prodrug in the resulting formulation may be greater than the solubility of the prodrug when added to a solution of the retaining solvent and oil.

Once the homogeneously dissolved solutions are formed by the preparative methods of the present invention, i.e., either by directly mixing the prodrug with the release-controlling solution or by pre-dissolving the prodrug in the retaining solvent, they may all be stable solutions. In some embodiments, the formulations prepared by pre-dissolving SDE in benzyl benzoate and then mixing with sesame oil are stable at 2-8° C. for at 24 months, and may remain homogeneous at about 0-4° C. while not forming precipitates or solid particles.

In some embodiments of the methods, the nalbuphine ester prodrug is SDE.

In some embodiments, step (a) may further include stirring the mixture of SDE and the oil-miscible retaining solvent for about 30 to 90 minutes, for example, for about 60 minutes. In some embodiments, step (b) may further include stirring the mixture of the resulting solution of step (a) and the oil for about 15 to 45 minutes, for example, for about 30 minutes. In some embodiments, step (a) and step (b) may be conducted at room temperature. The formulations of the present invention may be prepared without any heating process or other commonly used techniques to cause SDE to fully dissolve, by which a high purity of the resulting formulation can be achieved. Moreover, in some embodiments, only a short period of stirring is needed to prepare formulations of the present invention. Accordingly, the formulations of the present invention may be prepared in a more economical and convenient manner, which is beneficial to large-scale production.

In some embodiments of the methods, the oil-miscible retaining solvent may be benzyl benzoate, benzyl alcohol, or any mixture thereof, and the pharmaceutically acceptable oil may be sesame oil, cottonseed oil, castor oil, or any mixture thereof.

The present invention also provides a method for preparing a pharmaceutical formulation, comprising dissolving the nalbuphine ester prodrug in the oil-miscible retaining solvent; and mixing the resulting solution with the pharmaceutically acceptable oil to give a homogenous solution, wherein the formulation is suitable for administration by injection. In some embodiments, the nalbuphine ester prodrug is SDE; the concentration of SDE in the formulation is greater than about 70 mg/ml; the weight ratio of benzyl benzoate to sesame oil is about 0.8-1.2:1; and the formulation is suitable for administration by intramuscular or subcutaneous injection.

In some embodiments, the retaining solvent may be benzyl benzoate and the oil may be sesame oil, where the weight ratio of benzyl benzoate to the oil (the "BB/oil ratio") may be about 0.5 to about 16. In some embodiments, the BB/oil ratio is about 0.65 to about 3. In some embodiments, the BB/oil ratio is about 0.65 to about 2. In other embodiments, the BB/oil ratio is about 1-3 or about 1-2. In some embodiments, when the release period is predetermined to give a duration of action of about 5 or 6 days, the BB/oil ratio may be adjusted to about 1.1. Accordingly, when the release period is predetermined to give a duration of action of more than 6 days, the BB/oil ratio may be adjusted to more than about 1.1; and when the release period is predetermined to give a duration of action of less than 6 days, the BB/oil ratio may be adjusted to less than about 1.1.

The methods may each further comprise adding a solubilizing agent and/or a neutralizing agent. In some embodiments, the solubilizing agent and/or the neutralizing agent may be added to the release-controlling solution before the mixing with the prodrug. For example, the solubilizing agent and/or the neutralizing agent may be added to the release-controlling solution, and then mixed with the prodrug. Alternatively, the formulations may be prepared by mixing the prodrug with the mixture of the retaining solvent and the solubilizing agent and/or the neutralizing agent first, and then mixing with the oil.

The pharmaceutically acceptable oils, the oil-miscible retaining solvents, the solubilizing agents, and the neutralizing agents used in the methods of the present invention are the same as those described for the present formulations.

In some embodiments of the methods, the solubilizing agent may be an alkyl alcohol, such as ethanol, 1-propanol, 2-propanol, 1-butanol, and/or tert-butanol; and the nalbuphine ester prodrug may be SDE. In some embodiments, the solubilizing agent may be ethanol. The addition of the alkyl alcohol may significantly increase the solubility of SDE in the final formulations, by which a high drug loading formulation with a long release period can be achieved. In some embodiments, the alkyl alcohol may be used to increase the concentration of SDE in the final formulations to more than 100 mg/mL, for example, more than 150, 200, 250, or 300 mg/mL. In some embodiments, the alkyl alcohol may be used to increase the concentration of SDE in the final formulations by at least 30%. The alkyl alcohol may be added into the release-controlling solution before SDE is added into the solvent system. Alternatively, the alkyl alcohol may be added into the retaining solvent before SDE is mixed with the retaining solvent.

In some embodiments of the methods, the neutralizing agent may be a basic salt selected from the group consisting of trisodium citrate, disodium phosphate, sodium bicarbonate, and sodium lactate. The basic salt may be added into the formulation before or after mixing the prodrug with the release-controlling solution. Alternatively, the basic salt may be added into the formulation before or after the retaining solvent is mixed with the prodrug. Alternatively, the neutralizing agent may be mixed with the formulation prior to the administration of the present formulation.

In some embodiments, the methods of the present invention may further comprise filtering the homogenously dissolved solution with a bacteria proof filter, such as a Millipore 0.22 μm filter. The formulations of the present invention are homogeneously dissolved solutions without precipitates or solid particles, so that they can be easily sterilized by filtration with full or nearly full recovery of the drug.

Extended Release Periods/Lower Release Rates

In some embodiments, the present formulations provide extended release periods of nalbuphine ester prodrugs. For example, release rates/periods of nalbuphine ester prodrugs may be demonstrated or estimated through in vitro dissolution experiments designed to cause nalbuphine ester prodrug release from the formulations at a higher rate than the actual release rate in a living subject. When a formulation shows a lower dissolution rate in the dissolution experiments, it is expected that the formulation may have a longer release period (or a lower release rate) in a living subject. The dissolution rate may be defined as the amount of the prodrug, e.g., SDE, which goes into a dissolution medium from the formulation per unit time under certain conditions of interface, temperature and solvent composition. The dissolution of the nalbuphine ester prodrug can be determined by carefully dropping the formulation into a larger volume of a dissolution medium. For example, the volume of formulation may be 50-150 µl and the volume of dissolution medium may be 200-1000 ml, for example 500 ml. The dissolution medium may be a buffer with a surfactant, for example phosphate-buffered saline with 1% tween 80 and a pH of 6.0 (PBST). The dissolution medium can then be stirred and samples of the resulting medium can be withdrawn at predetermined time intervals. Prior to termination of the experiment, HCl can be added to the resulting medium to allow 100% release of the nalphubine ester prodrug and a sample can be taken and used as a reference point of 100% in calculating the release rate of the nalbuphine ester prodrug. The nalbuphine ester prodrug can be SDE. For example, the dissolution profile of a formulation can be determined as described in Example 1.

In some embodiments, when the retaining solvent/oil ratio is about 0.5, about 0.65, about 1, about 2, about 3, and about 16, the time for releasing about 50% of the total amount of the nalbuphine ester prodrug from the formulation into the in vitro medium may be about 15-25 minutes, about 20-30 minutes, about 35-45 minutes, about 50-60 minutes, about 85-95 minutes, and about 120-130 minutes, respectively. It is demonstrated that when the retaining solvent/oil ratio is increased, the dissolution rate of the prodrug from the formulation may be decreased. The lower in vitro dissolution rate of a formulation may reflect a longer release period in a living subject (or a lower in vivo release rate).

The release rates/periods of the present formulations, or the aforesaid correlation between the in vitro dissolution rate and the in vivo release period/release rate, may be further assessed or verified by evaluating the in vivo availability and pharmacokinetic parameters of nalbuphine after administration of a present formulation to a living subject. For example, a nalbuphine ester prodrug formulation of the present invention can be administered to a living subject through an injection. The nalbuphine ester prodrug can be SDE. In some embodiments, the injection may be subcutaneous. In other embodiments, the injection may be intramuscular. The subject may be an animal, for example a dog, cat, or rodent, or the subject may be a human. Blood samples may be taken from the subjects prior to formulation administration and at various time points following administration of the formulation, such as over the first 144 or 360 hours after administration. For example, blood samples may be drawn at 1, 2, 6, 24, 36, 48, 60, 72, 96, 120 and 144 hours after administration. Alternatively, blood samples may be drawn at 0.083, 0.25, 0.5, 1, 1.5, 2, 3, 4, 6, 8, 12, and 24 hours after administration or at similar intervals after administration, and at regular intervals for up to 12 days after administration. The whole blood or plasma concentration of nalbuphine can then be determined for the blood samples. For example, plasma and whole blood concentrations of nalbuphine can be determined as described in Examples 3 and 4.

In some embodiments, when the retaining solvent/oil ratio is adjusted to about 0.65, about 99% of the prodrug may be released from the formulation at 144 hours from dosing; when the retaining solvent/oil ratio is adjusted to about 1, about 90% of the prodrug may be released from the formulation at 144 hours from dosing; when the retaining solvent/oil ratio is adjusted to about 2, about 80% of the prodrug may be released from the formulation at 144 hours from dosing. It is shown that when the retaining solvent/oil ratio is increased, the in vivo release period of the formulation may be extended or prolonged, which is consistent with the results demonstrated by the in vitro dissolution experiments.

In some embodiments, when the retaining solvent/oil ratio is adjusted to about 1, e.g., 1.12, the present formulation may have a release period of equal to or greater than about 10 days, 12 days and 14 days and a duration of action of equal to or greater than about 5 or 6 days. In some embodiments, the retaining solvent/oil ratio may be adjusted to lower than about 1, e.g., 0.65, to give a formulation having a duration of action of less than 6 days, for example, about 4 days. In other embodiments, the retaining solvent/oil ratio may be adjusted to more than about 1.1, e.g., 2, to give a formulation having a duration of action of equal to or greater than about 5 days and 6 days, for example, more than 6 days.

In one embodiment, a pharmaceutical formulation of the present invention is administered intramuscularly into a subject in need thereof for pain relief and the plasma or whole blood concentration of nalbuphine may reach no less than 1 ng/mL within 6-12 hours of dosing and this concentration may remain for equal to or greater than 12 days from administration. In one embodiment, the plasma or whole blood concentration of nalbuphine may reach no less than 3 ng/mL within 12-24 hours of dosing and this concentration of nalbuphine may be maintained for equal to or greater than 7 days from dosing. In another embodiment, the plasma or whole blood concentration of nalbuphine may reach no less than 3 ng/mL within 12-24 hours of dosing, and maintain at said concentration for equal to or greater than 9 days from dosing.

Pharmacokinetic parameters may also be calculated from the whole blood or plasma nalbuphine concentrations, for example, the maximum observed nalbuphine concentration in the plasma or whole blood ($C_{max}$) may be determined. The time to $C_{max}$ ($T_{max}$), half-life ($T_{1/2}$), mean residence time (MRT), and the area under the curve (time zero to the last quantifiable nalbuphine measurement ($AUC_{0-t}$) and time zero extrapolated to infinity ($AUC_{0-inf}$)) may also be determined. For example, plasma and whole blood concentrations of nalbuphine and the pharmacokinetic parameters of the present formulations can be determined as described in Examples 3 and 4.

After administration via intramuscular injection to a subject, in some embodiments the formulations of the present invention exhibit the following in vivo characteristics: (a) a peak plasma level of nalbuphine occurs within 45-66 hours after administration ($T_{max}$); and (b) an average elimination half-life ($T_{1/2}$) of nalbuphine after administration is about 56-90 hours.

In some embodiments, the plasma or whole blood concentrations of nalbuphine following administration may be used to determine the onset of the analgesic effect and the duration of action of the present formulations. For example, the obtained plasma or whole blood concentrations of nalbuphine may be compared to a concentration of plasma or whole blood nalbuphine that has been reported to exhibit analgesic effects. In general, by administration of a pharmaceutical formulation of this disclosure via intramuscular injection, the onset of the analgesic effect may take place in about 6 to 36 hours of dosing and the duration of action may be about 6 to about 12 days. In some embodiments, the duration of action may be equal to or greater than about 5 days, about 6 days, about 9 days, or about 12 days. In some embodiments, the duration of action may be equal to or greater than 3, 6, 9, 10, 12, or 14 days. In some embodiments, the duration of action of the formulation is equal to or greater than about 5 or 6 days. In other embodiments, the duration of action of the formulation is equal to or greater than about 7 days. The time of onset for an analgesic effect can depend on dosing, the individual's response, and the type of pain relief sought.

In certain embodiments, the present formulation is prepared with a BB/oil ratio of about 0.8-1.2, wherein the SDE concentration is about 75 mg/mL. In some embodiments, such formulations may maintain a blood concentration of nalbuphine at >3 ng/mL for equal to or greater than about 6 days, or at >1 ng/mL for equal to or greater than about 12 days, when a single dose of 150 mg of SDE is administered. Formulations with an increased BB/oil ratio may have a duration of action for more than 6 days. Similarly, if the formulation is intended to provide a duration of action shorter than 6 days, e.g., 3 or 5 days, the BB/oil ratio may be decreased.

It should be understood that the duration of action of the present formulation may depend not only on the retaining solvent/oil ratio, but also the concentration of the prodrug in the formulation, and the total dose being administered. The concentration of the prodrug in the formulation, and the total dose being administered may be adjusted per need, so as to provide an effective blood concentration for a desired period.

Treatment of Pain

In another aspect, the present invention provides methods for treating pain, comprising administering a therapeutically effective amount of the pharmaceutical formulation of the present invention to a subject in need thereof. In some embodiments, the present invention provides methods for treating post-surgical pain or other types of long-term pain by the present formulations. In some embodiments, the pharmaceutical formulation is administered by intramuscular or subcutaneous injection. Treatment of pain can be evaluated by assessing a subject's assessment of pain on an intensity scale. For example, the Visual Analog Scale (VAS) for pain can be used to score a subject's pain intensity (Psychol) Med. 1988 November; 18(4):1007-19). The pain VAS is a unidimensional intensity scale on which the subject is asked to indicate his or her level of pain intensity. For example, pain intensity may be assessed started right before the first use of patient-controlled analgesia (PCA), and at 1±0.1, 2±0.1, 3±0.1, 4±0.25, 8±0.5, 12±0.5, 16±0.5, 20±0.5, 24±1, 28±1, 32±2, 36±2, 40±2, 44±2, 48±2 hours after the surgery, and be assessed during Days 3-7 in the morning and evening, as well as during special events such as bowel movements. For example, the patient-controlled analgesic is ketorolac. In some embodiments, the present formulations may be administered to a subject prior to a surgical procedure. For example, the surgical procedure may be a hemorrhoidectomy. In certain embodiments, the present formulations may be administered 6-36 hours prior to surgery. In some embodiments, 150 mg of SDE is administered prior to surgery. Pain intensity can then be assessed following surgery, for example for 48 hours after surgery. In some embodiments, pain can be assessed with the VAS pain scale. In some embodiments, subjects administered a present formulation have a lower VAS pain score over 48 hours than subjects administered a placebo. For example, evaluation of the treatment of pain can be determined as described in Example 4.

Treatment of pain can also be assessed by evaluating a subject's use of a post-surgical analgesic, i.e. a rescue medicine, such as ketorolac. For example, the time of a subject's first use of the post-surgical analgesic following surgery can be evaluated. In some embodiments, subjects administered a present formulation prior to surgery have a longer period of time before the post-surgical analgesic use compared to subjects administered a placebo. For example, treatment of pain can be assessed as described in Example 4.

Treatment of pain can also be assessed by evaluating a subject's effective blood concentration of nalbuphine after administration of the present formulation. In some embodiments, when the retaining solvent/oil ratio is increased, the time to reach the effective blood concentration of nalbuphine may be longer, thus the onset of action of the formulation may be slower. Accordingly, the time to administer the formulation into a subject in need may be adjusted per the desired onset of action of the formulation. For example, when the retaining solvent/oil ratio is about 0.65, about 1, or about 2, the blood concentration of nalbuphine at 1 hour after administration may be about 28 ng/mL, about 11 ng/mL, or about 7 ng/mL, respectively. In some embodiments, for example, if the effective blood concentration of nalbuphine in a living subject, e.g., a dog, is about 5 ng/mL, the formulation having a retaining solvent/oil ratio of about 2 may be administered to the subject about 1 hour prior to the onset of pain symptom; while the formulation having a retaining solvent/oil ratio of about 0.65 may be administered to the subject about 30 minutes prior to the onset of pain symptom.

In some embodiments, the present methods for treating pain comprises administering to a subject, e.g., a human, in need thereof the formulation of the present invention having a retaining solvent/oil ratio of about 0.8-1.2, e.g., about 1.12, at 6 to 36 hours prior to the onset of pain symptoms, wherein the formulation is administered to the subject via intramuscular injection. In some embodiments, the formulation having a retaining solvent/oil ratio of about 1.12 may be administered 12 to 36 hours prior to the onset of pain symptoms. In some other embodiments, the formulation having a retaining solvent/oil ratio of about 1.12 may be administered 12 to 24 hours prior to the onset of pain symptoms. In some embodiments, the concentration of SDE in the formulation is about 75 mg/mL, and such formulation is administered with a total dose of up to 150 mg of SDE.

In some embodiments, the present methods for treating pain comprises administering to a subject, e.g., a dog, in need thereof the formulation of the present invention having a retaining solvent/oil ratio of about 1.18. In one embodiment, the concentration of SDE in the formulation is about 80 mg/mL, and such formulation is administered with a total dose of up to 160 mg of SDE.

In some embodiments, the present method is for treating post-surgical pain, wherein the onset of pain symptom is during or after a surgical operation on the subject. Examples of the surgical operation include common types of general surgery, such as hernia surgery, hemorrhoid surgery, abdominal surgery, obstetric and gynecological surgery, plastic surgery, orthopedic surgery, otolaryngology surgery, male genital procedures, and dental surgery. In some embodiments, the surgical operation is hemorrhoid surgery. In certain embodiments, the formulation having a retaining solvent/oil ratio of about 1.12 is administered 12 to 36 hours prior to the surgical operation. In some embodiments, the formulation having a retaining solvent/oil ratio of about 1.12 is administered 12 to 24 hours prior to the surgical operation. In some embodiments, the formulation being administered contains SDE, sesame oil and benzyl benzoate, where the weight ratio of benzyl benzoate to sesame oil is about 0.8-1.2:1; and the concentration of SDE in the formulation is about 75 mg/mL. In certain embodiments, a formulation having a retaining solvent/oil ratio of about 1.12 is administered to a human with a total dose of up to 150 mg of SDE.

Another aspect of the present invention is to provide a method of treating long-term pain, which includes administering to a subject in need thereof via intramuscular injection a pharmaceutical formulation of the present invention having a retaining solvent/oil ratio of about 1.12 at 6-36 hours prior to the onset of pain symptoms. Examples of the long-term pain include labor pain, chronic back pain, and chronic joint pain. In some embodiments, the formulation having a retaining solvent/oil ratio of about 1.12 is administered about 12-36 hours prior to the onset of pain symptoms. In certain embodiments, the formulation having a retaining solvent/oil ratio of about 1.12 is administered with a total dose of up to 150 mg of SDE.

In some embodiments, the formulation is prepared with a retaining solvent/oil ratio of about 0.8-1.2 and a SDE concentration of about 75 mg/mL, and is intramuscularly administered with a total dose of up to about 150 mg of SDE. In such case, the onset of action of the formulation may be within about 6-36 hours, or about 12-36 hours, from dosing; and the duration of action of the formulation may be about 6 days, about 7 days, or about 9 days. In other embodiments, the formulation is prepared with a retaining solvent/oil ratio of about 0.65 and a SDE concentration of about 50 mg/mL, and is intramuscularly administered with a total dose of up to about 160 mg of SDE. In other embodiments, the formulation is prepared with a retaining solvent/oil ratio of about 2 and a SDE concentration of about 80 mg/mL, and is intramuscularly administered with a total dose of up to about 160 mg of SDE.

In some embodiments, the formulation is administered at a concentration of about 50-160 mg/ml, or about 70-100 mg/mL, with a total administered dose of about 75-160 mg, or about 150-160 mg. For example, the concentration may be about 50, 75, 80, 100, or 150 mg/mL; and the total dose may be about 75, 100, 125, 150, or 160 mg. In certain embodiments, the formulation is administered at a concentration of about 75 mg/ml and a total dose of about 150 mg. In other embodiments, the formulation is administered at a concentration of about 50 mg/mL, or about 80 mg/ml, and a total dose of about 160 mg.

EXAMPLES

Example 1

In Vitro Release Study of Present Formulations with Various BB/Oil Ratio (1) Preparation of the Present Formulations Eight present formulations with various SDE concentrations (50-150 mg/mL) and various weight ratios of benzyl benzoate to sesame oil ("BB/oil ratio"), or the mixture of benzyl benzoate and benzyl alcohol to sesame oil ("BB+BA/oil ratio") (0.5-19) were prepared based on Table 1A and Table 1B. Among them, AF4, R2, N7 and N9 formulations were prepared according to the following Method A.

Method A:

The solvent systems (i.e., the mixture of benzyl benzoate, with or without benzyl alcohol, and sesame oil) were respectively prepared by mixing each component with the predetermined volume corresponding to the desired weight/weight percent (w/w %) listed in Table 1A and Table 1B. The resulting solvent mixtures were vortexed or stirred at room temperature to fully mix each component. The predetermined amounts of SDE were respectively weighed, based on the SDE concentrations listed in Table 1A and 1B, and then added into volumetric flasks containing the corresponding solvent mixtures. The resulting mixtures were fully mixed by inverting and shaking the volumetric flasks to give the final formulations.

R1, AF1, AF3 and N8 formulations were prepared according to the following Method B.

Method B:

The predetermined amounts of SDE were respectively weighed, based on the SDE concentrations listed in Table 1A and Table 1B, and then added into benzyl benzoate, or the mixture of benzyl benzoate and benzyl alcohol, of predetermined volume corresponding to the desired weight/weight percent (w/w %) listed in Table 1A and Table 1B. The resulting mixtures were mixed by vortexing or stirring to fully dissolve SDE. Sesame oil of predetermined volume was then added into the resulting mixtures of benzyl benzoate, or the mixture of benzyl benzoate and benzyl alcohol, and SDE to give the final formulations.

TABLE 1A

The present formulations having various BB/oil ratios

| Sample No. | Benzyl benzoate (w/w %) | Sesame oil (w/w %) | SDE (mg/mL) | BB/oil ratio |
|---|---|---|---|---|
| R1 | 33 | 67 | 50 | 0.5 |
| AF3 | 39 | 61 | 50 | 0.65 |
| AF1 | 54.2 | 45.8 | 80 | 1.18 |
| AF4 | 67 | 33 | 80 | 2 |
| R2 | 75 | 25 | 75 | 3 |
| N7 | 94 | 6 | 150 | 16 |

TABLE 1B

The present formulations having various BB + BA/oil ratios

| | Benzyl benzoate + Benzyl alcohol (w/w %) | Sesame oil (w/w %) | SDE (mg/mL) | BB + BA/oil ratio |
|---|---|---|---|---|
| N8 | 45 | 55 | 75 | 0.82 |
| N9 | 95 | 5 | 150 | 19 |

(2) In Vitro Dissolution Experiment:

The following in vitro dissolution experiment and UPLC analysis were performed on the formulations listed in Table 1A and Table 1B.

The dissolution/release rate of SDE from each of the formulations was respectively assessed by in vitro dissolution experiment. The dissolution medium was a PBST buffer (pH6.0) with 0.1% tween 80. For each experiment, 500 mL medium was placed in a 600 mL beaker and the air bubble on the top was removed. 50-150 μl of each SDE formulation listed in Table 1A and Table 1B was respectively and carefully dropped into the medium (in each experiment, the dropped formulation contained the same amount of SDE, i.e. about 7.5 mg). The temperature of the medium was set at room temperature (about 25-28° C.), and the stir speed was set at about 360 rpm. 5 mL of the resulting medium was withdrawn at predetermined time intervals. 200 μl 6N HCl was added into the resulting medium 20 minutes before the termination point of the experiment to allow 100% release of SDE at an acidic condition. 5 mL of the resulting medium at the termination point was collected and taken as the reference point of 100% release in calculating the dissolution rate of SDE at each of the time intervals.

UPLC Analysis

The concentration of SDE in each of the samples collected in the in vitro dissolution experiment was determined by ultra performance liquid chromatography (UPLC). Standard solutions were prepared. UPLC analysis was conducted by using the ACQUITY UPLC ethylene bridged hybrid (BEH) C18, 1.7 μm, 2.1*50 mm column under the following conditions:

| | |
|---|---|
| Flow rate | 0.1 mL/min |
| Injection volume | 10 μl |
| Run time | 15 minutes |
| Detector | UV 280 nm |
| Column temperature | 35° C. |
| Sample temperature | 15° C. |
| Mobile phase | Buffer A*/methanol = 40/60 |

*Buffer A: acetate buffer.

Figure 1B:
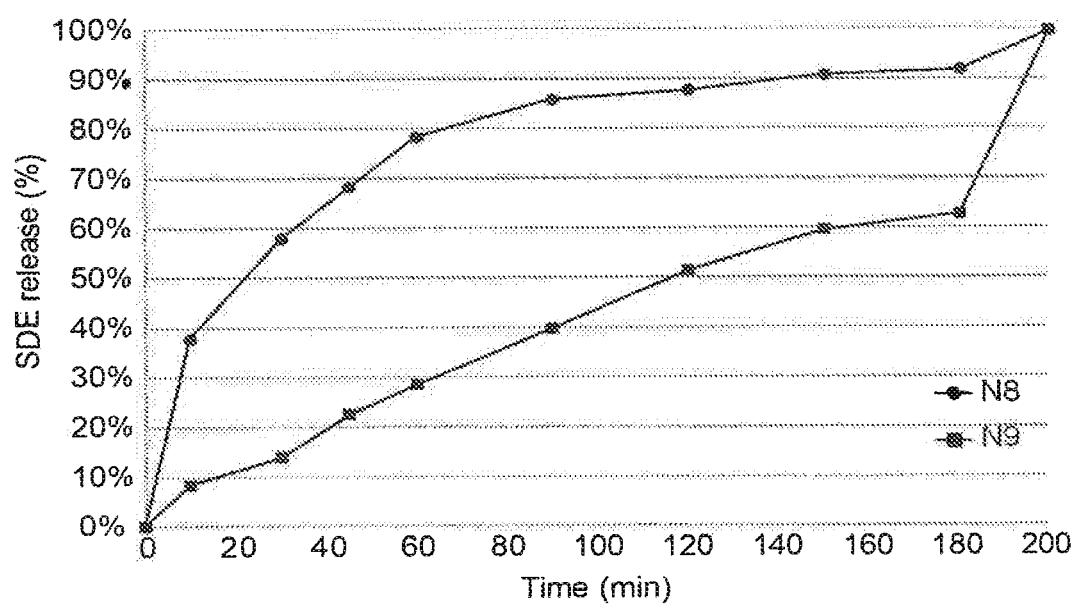
FIG. 1B shows the accumulated dissolution profiles of N8 and N9 formulations.

The accumulated SDE dissolution profiles of each of the formulations are plotted in FIG. 1A and FIG. 1B.

In FIG. 1A, it can be seen that when the BB/oil ratio is increased from 0.5 to 16, the dissolution rate of SDE from the formulation is decreased, i.e. the release period of SDE from the formulation is extended. For example, when the BB/oil ratio was about 0.5 (R1), the time required for releasing about 50% of the total amount of SDE from the formulation into the in vitro medium was about 15-25 minutes; when the BB/oil ratio was about 3 (R2), the time required for releasing 50% of the total amount of SDE from the formulation into the in vitro medium was about 85-95 minutes; and when the BB/oil ratio was about 16 (N7), the time required for releasing 50% of the total amount of SDE from the formulation into the in vitro medium was about 120-130 minutes. In FIG. 1B, it can be seen that the trend observed in FIG. 1A still exists when the retaining solvent is the mixture of benzyl benzoate and benzyl alcohol.

The results indicate that the in vitro release rate/release period of SDE from the present formulations may be regulated or controlled by the retaining solvent/oil ratio, e.g., the BB/oil ratio, of the solvent system. When a longer release period is intended, the retaining solvent/oil ratio in the formulation can be increased per need.

Correlations between in vitro and in vivo data are often used during pharmaceutical development in order to reduce development time and optimize the formulation. Many studies reported in the late '70s and early '80s established the basic reliability of such correlations (Pharm.Res.1990, 7,975-982). Various definitions of in vitro-in vivo correlation have been proposed as a predictive mathematical model describing the relationship between an in vitro property of an extended release dosage form (usually the rate or extent of drug dissolution or release) and a relevant in vivo response, e.g., plasma drug concentration or amount of drug absorbed. Under this concept, it is believed that when the retaining solvent/oil ratio of the present formulations is increased, the formulation may have an increased/prolonged in vivo release period.

Example 2

Comparison Between Method A and Method B (1) Suspensions with Precipitates, Prepared by Method A when the BB/Oil Ratio is about 1

Two samples (1 and 2) were prepared by directly adding SDE into a mixture of sesame oil and benzyl benzoate (i.e., Method A of Example 1). In Sample 1, 5.5 mL sesame oil and 4.5 mL benzyl benzoate were first mixed to form an oily solvent mixture. 750 mg of SDE was then added into the solvent mixture. The resultant mixture was sonicated for at least 2 hours, left overnight at room temperature, and then centrifuged for 10 minutes at 3000 rpm. The upper clear solution was collected and then subjected to high performance liquid chromatography (HPLC) analysis. Sample 2 was prepared by following the process for preparing Sample 1 except that the amount of SDE was changed to 1000 mg. For Samples 1 and 2, the ratios of "the originally added weight of SDE" to "the volume of benzyl benzoate and sesame oil" were 75 mg/mL and 100 mg/mL, respectively. For both of Samples 1 and 2, suspensions with precipitates were formed immediately after SDE was added into the oily mixture. After being sonicated for over 2 hours and left overnight at room temperature, visible solid particles of SDE were still present in the resulting mixtures.

(2) Homogeneous Solutions, Prepared by Method B when the BB/Oil Ratio is about 1

Four samples (3-6) were prepared according to Method B of Example 1. Specifically, in Sample 3, 2.25 mL of benzyl benzoate and 375 mg of SDE were first mixed and stirred to form a clear solution. 2.75 mL of sesame oil was then added into the clear solution to give a homogeneous solution (resulting SDE concentration of 75 mg/mL; volume ratio of benzyl benzoate to sesame oil being 45:55), such that the SDE is homogenously dissolved in the solution. Sample 4 was prepared by following the method for making Sample 3 except that 2 mL benzyl benzoate and 3 mL sesame oil were used (resulting SDE concentration of 75 mg/mL; volume ratio of benzyl benzoate to sesame oil being 40:60). Sample 5 was prepared by following the method for making Sample 3 except that 2.5 mL benzyl benzoate and 2.5 mL sesame oil were used (resulting SDE concentration of 75 mg/mL; volume ratio of benzyl benzoate to sesame oil being 50:50). Sample 6 was prepared by following the process of making Sample 3 except that 500 mg SDE was used (resulting SDE concentration of 100 mg/mL; volume ratio of benzyl benzoate to sesame oil being 45:55). Samples 3-6 were then subject to a freeze-thaw test to check their physical stabilities. The freeze-thaw test was conducted by cooling each of the samples at about 0-4° C. for about 12 hours, warming each of the cooled samples at room temperature for about 12 hours, and sequentially repeating the cooling and warming steps twice. All of Samples 3-6 stayed clear and homogeneous after the freeze-thaw test. The resulting samples were centrifuged for 10 minutes at 3000 rpm. The upper solution of each sample was respectively collected and then subjected to HPLC analysis.

(3) HPLC Analysis of Samples 1-6

The HPLC analysis was conducted using the column Waters Xbridge RP18, 4.6 mm×250 mm, 3.5 μm column (Part No.: 186003964) and the following conditions:

Flow rate: 0.6 ml/min
Injection volume: 10 μl
Run Time: 70 minutes
Detector: UV wavelength 280 nm
Column temperature: 35° C.
Sample temperature: 25° C.
Gradient program:

| Time (mins.) | Mobile phase A % | Mobile phase B % |
|---|---|---|
| 0 | 50 | 50 |
| 30 | 30 | 70 |
| 60 | 30 | 70 |
| 62 | 50 | 50 |
| 70 | 50 | 50 |

Mobile phase A was an acetate buffer, and Mobile phase B was methanol. 1.0 mL of each of the upper solutions from centrifuged Samples 1-6 was collected and then diluted with acetonitrile to 100 mL. The resulting solutions were subjected to the HPLC analysis, individually and separately. The results of the HPLC analysis were used to calculate the concentration of dissolved SDE in centrifuged Samples 1-6, and the data is summarized in Table 2.

TABLE 2

Comparison between the formulations prepared by Method A and Method B.

| Sample # | BB/oil ratio | Appearance | Added SDE concentration (mg/mL) | Calculated SDE Concentration (mg/mL) |
|---|---|---|---|---|
| Samples prepared according to Method A: | | | | |
| 1 | 1.0:1 | Suspension | 75 | 60 |
| 2 | 1.0:1 | Suspension | 100 | 65 |
| Samples prepared according to Method B: | | | | |
| 3 | 1.0:1 | Clear solution | 75 | 73 |
| 4 | 0.8:1 | Clear solution | 75 | 76 |
| 5 | 1.2:1 | Clear solution | 75 | 78 |
| 6 | 1.0:1 | Clear solution | 100 | 102 |

In Table 2, the weight ratio of benzyl benzoate to sesame oil is calculated by the following formula:

Weight ratio=Volume ratio*1.118/0.917

In the formula, 1.118 (g/cm$^3$) represents the density of benzyl benzoate, and 0.917 (g/cm$^3$) represents the density of sesame oil. "Added SDE concentration" represents the ratio of "the originally added weight of SDE" to "the originally added volume of benzyl benzoate and sesame oil." "Calculated SDE Concentration" represents the calculated SDE concentration of Samples 1-6, obtained by centrifuging each of the samples, and then analyzing the resulting supernatants by HPLC.

It can be seen from Table 2 that, when the BB/oil ratio is set to about 1, samples prepared according to Method A—i.e., Samples 1 and 2—were all in the form of suspension with precipitates, while samples prepared according to Method B—i.e., Samples 3-6—were all in a homogeneous solution form. For Samples 1 and 2, the difference between "Added SDE concentration" and "Calculated SDE Concentration" indicates that more than 20% of SDE formed solid particles in the formulations, which had greatly exceeded the limitation of "at most 0.5-5.0% solids" acceptable for an intramuscular injection suspension (see R. M. Patel, Parenteral Suspension: an Overview, *Int. J. Curr. Pharm. Res.,* 2010, 2,3:3-13). In addition, the visible solid particles indicated that the average particle size of Samples 1 and 2 was much larger than 5 micrometer (i.e., the upper limit for a qualified intramuscular injection suspension). Moreover, "Calculated SDE Concentration" of Samples 1 and 2 indicated that the saturated concentration of SDE in the formulations prepared by Method A, when the BB/oil ratio is set to about 1, was around 60-65 mg/mL.

For Samples 3-6, it can be seen that the difference between "Added SDE concentration" and "Calculated SDE Concentration" was not significant, meaning the homogeneous formulations prepared by Method B were stable even after being tested by three cycles of freeze-thaw step. The above data also demonstrate that when the weight ratio of benzyl benzoate to sesame oil was in the range of about 0.8-1.2:1, the present formulations prepared by Method B can be homogeneous and stable with an SDE concentration of 100 mg/mL or less. In some embodiments, the present invention may form a homogeneous and stable formulation, at the BB/oil ratio of about 0.8-1.2:1, having a SDE concentration of 70-100 mg/mL, for example, 75 mg/mL. The SDE concentration of more than 70 mg/mL allows the injection volume to be greatly reduced, as compared with the injection volume suggested by the prior art.

It should be understood that when the BB/oil ratio is increased, for example, from about 1 to about 1.5, the solubility of SDE in the mixture of BB and oil will be increased significantly, for example, from about 60 mg/mL to about 150 mg/mL. Therefore, a homogeneously dissolved formulation having a BB/oil ratio of about 1.5 can be prepared by either Method A or Method B if the intended SDE concentration is lower than 150 mg/mL. However, when a formulation having a BB/oil ratio of about 1.5 needs to be prepared with a SDE concentration of greater than 150 mg/mL, Method B must be used to achieve a homogeneously dissolved formulation.

Example 3

In Vitro and In Vivo (on Dogs) Studies of Present Formulations (1) Preparation of Present Formulations Three SDE formulations (AF3, AF1, and AF4) were prepared based on the concentrations and BB/oil ratios listed in Table 3. AF4 was prepared according to Method A of Example 1; AF3 and AF1 were prepared according to Method B of Example 1.

TABLE 3

Present formulations for in vitro and in vivo studies on dogs

| Sample No. | Benzyl benzoate (w/w %) | Sesame oil (w/w %) | SDE (mg/mL) | BB/oil ratio |
|---|---|---|---|---|
| AF3 | 39 | 61 | 50 | 0.65 |
| AF1 | 54.2 | 45.8 | 80 | 1.18 |
| AF4 | 67 | 33 | 80 | 2 |

(2) Stability of Present Formulation

AF3, AF1 and AF4 formulations were then subject to a freeze-thaw test to check its physical stabilities. The freeze-thaw test was conducted by cooling each of the samples at about 0-4° C. for about 12 hours, warming each of the cooled samples at room temperature for about 12 hours, and sequentially repeating the cooling and warming steps twice. AF3, AF1, and AF4 formulations stayed clear and homogeneous after the freeze-thaw test. The resulting samples were centrifuged for 10 minutes at 3000 rpm. The upper solution of each sample was respectively collected and then subjected to UPLC analysis according to the method of Example 1, except that the run time was 15 minutes and the sample volume was 1 ul. "Added SDE concentration" and "Calculated SDE Concentration" are the same as that defined in Example 2, except that the upper solutions of AF3, AF1 and AF4 were analyzed by UPLC rather than HPLC.

TABLE 4

UPLC analysis results of AF3, AF1 and AF4 formulations

| Sample No. | BB/oil ratio | Appearance | Added SDE concentration (mg/mL) | Calculated SDE Concentration (mg/mL) |
|---|---|---|---|---|
| AF3 | 0.65:1 | Clear solution | 50 | 47 |
| AF1 | 1.18:1 | Clear solution | 80 | 77 |
| AF4 | 2:1 | Clear solution | 80 | 79 |

In Table 4, it can be seen that the difference between "Added SDE concentration" and "Calculated SDE Concentration" is not significant, meaning the 3 formulations are homogeneous, and are stable even after being subjected to three freeze-thaw cycles. The three formulations are respectively prepared by Method A or Method B to form a homogeneous solution without solid particles, and the homogeneous solutions exhibit superior stability that can satisfy commercial needs, such as being suitable for direct sterilization by filtration and low temperature storage (shelf-life may be prolonged when being stored at a lower temperature).

(3) In Vitro Dissolution Experiment

Figure 2:
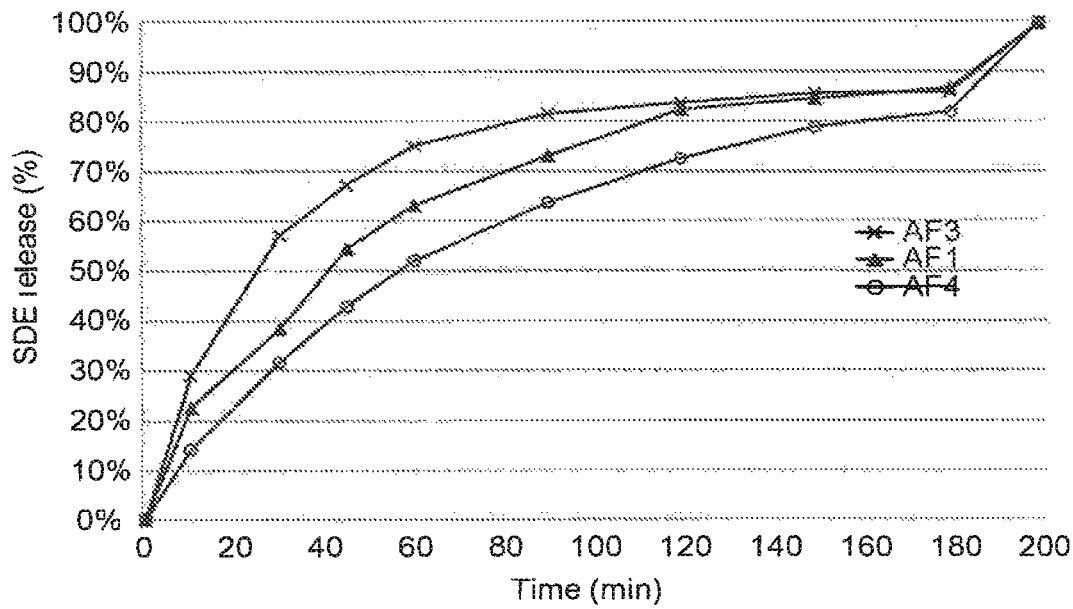
FIG. 2 shows the accumulated dissolution profiles of AF3, AF1 and AF4 formulations.

In vitro dissolution experiments and UPLC analyses were performed, according to the processes disclosed in Example 1, on AF3, AF1 and AF4 formulations. The accumulated SDE dissolution profiles of each of the formulations are plotted in FIG. 2. It can be seen from FIG. 2 that, when the BB/oil ratio is about 0.65, the time required for releasing 50% of the total amount of SDE from AF3 formulation into the in vitro medium was about 20-30 minutes. When the BB/oil ratio was about 1.18, the time required for releasing 50% of the total amount of SDE from AF1 formulation into the in vitro medium was about 35-45 minutes. When the BB/oil ratio was about 2, the time required for releasing 50% of the total amount of SDE from AF4 formulation into the in vitro medium was about 50-60 minutes. This testing indicates that when the BB/oil ratio is increased from 0.65 to 2, the in vitro dissolution rate of the present formulation will be decreased.

(4) Determining the Effective Plasma Nalbuphine Concentration for Analgesia in Dogs In the Handbook of Veterinary Pain Management (2nd Edition, 2009), the potencies of nalbuphine and other opioid analgesics were reported (page 167, Table 9-2). The duration of analgesia when administrating nalbuphine at 0.5 mg/kg on dogs was reported to be about 4 hours. Thus, the plasma concentration of nalbuphine at 4 hours after injection of the said dose of nalbuphine via subcutaneous administration may be the lowest effective plasma concentration of nalbuphine for analgesia on dogs. According to in vivo experiments conducted by the inventors, the average plasma concentrations of nalbuphine at 3 hours and 4 hours after subcutaneously injected with 0.5 mg/kg nalbuphine were 9.9 ng/mL and 5.2 ng/mL, respectively. Therefore, it may be regarded that the effective plasma concentration of nalbuphine for analgesia in dog is about 5 ng/mL.

(5) Intramuscular Administration of Present Formulations into Dogs

An animal study was conducted to verify the correlation between the in vitro dissolution rate and the in vivo release rate/release period of the present formulations. Each of the AF3, AF1, and AF4 formulations were separately administered to two male Beagle dogs by intramuscular injection. The dose of SDE was 160 mg for each dog, and the injection volumes varied according to the drug concentration of each formulation (AF3: 3.2 mL, AF1 and AF4: 2 mL). The blood samples were drawn prior to the dosing, and at 1, 2, 6, 24, 36, 48, 60, 72, 96, 120 and 144 hours after dosing. The plasma nalbuphine concentration of each sample was determined using a liquid chromatography-mass spectroscopy/mass spectroscopy (LC-MS/MS) system consisting of an AB AP14000 triple-quadrupole mass spectrometer coupled with Shimazdu LC-20AD and a CTC AutoSampler.

Figure 3:
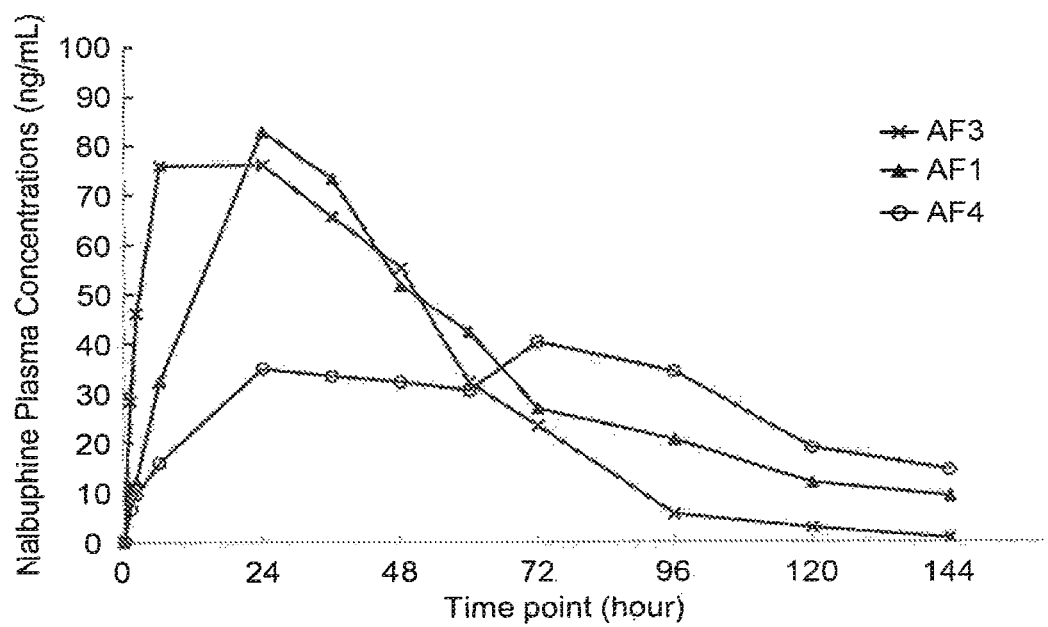
FIG. 3 shows the plasma nalbuphine concentration in dogs after intramuscular injection of AF3, AF1 and AF4 formulations (total dose: 160 mg/dog).
Figure 4:
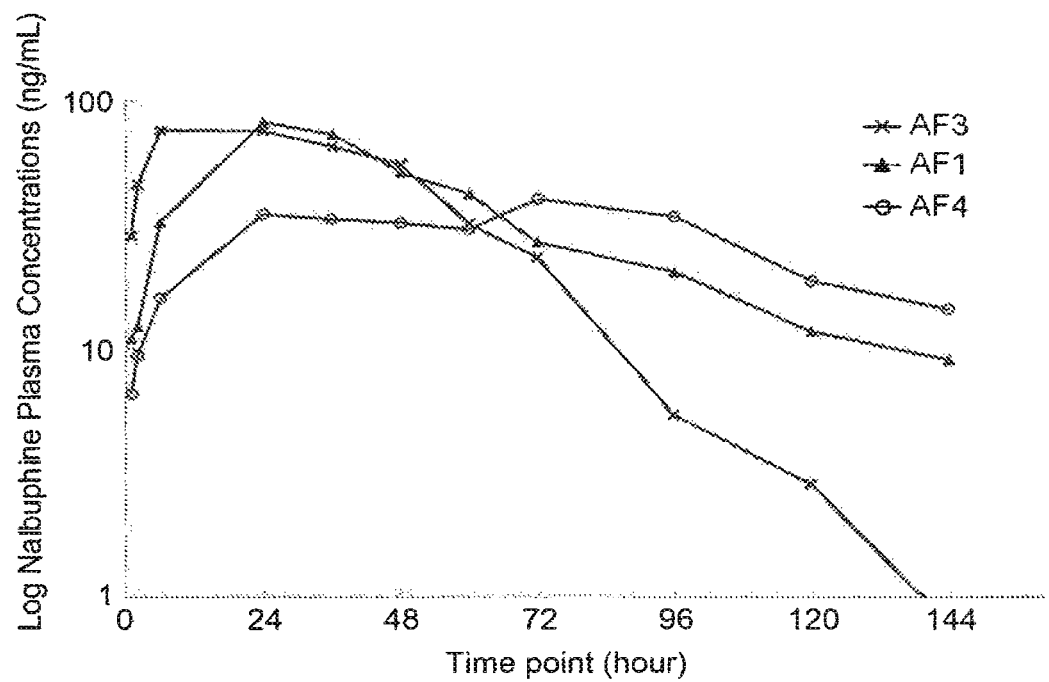
FIG. 4 shows the log plasma nalbuphine concentration in dogs after intramuscular injection of AF3, AF1 and AF4 formulations (total dose: 160 mg/dog).

The mean plasma concentration-time profiles of nalbuphine from Day 1 to Day 6 for the three formulations are showed in FIG. 3, and the corresponding log concentration-time profiles are shown in FIG. 4. Since SDE is rapidly converted into nalbuphine when released from the formulation into the blood or tissues, the plasma nalbuphine concentration is measured to represent the release amount of SDE from the formulation.

The in vivo testing results of the AF3, AF1 and AF4 formulations on dogs are consistent with the trend we expect based on the in vitro dissolution studies. It can be seen from FIG. 3 that when the BB/oil ratio is increased, the in vivo release period of the formulation is extended or prolonged. More specifically, the nalbuphine plasma concentrations at 144 hours (Day 6) after administration of AF3, AF1 and AF4 are about 0.4 ng/mL, about 9.2 ng/mL and about 14.7 ng/mL, respectively. Based on an assumption that the effective plasma concentration of nalbuphine for analgesia on dog is about 5 ng/mL, AF3 formulation would not produce an analgesic effect at 144 hours from dosing, while the AF1 and AF4 formulations would produce an analgesic effect for a period longer than 144 hours from dosing. According to the result of dog experiment, when the BB/oil ratio was adjusted to lower than about 1, e.g. 0.65, the formulation may have a duration of action of less than 6 days, for example, about 4 days; when the BB/oil ratio was adjusted to greater than about 1, e.g. 2, the formulation may have a duration of action of equal to or greater than about 5, for example, more than 6 days. Thus, an extended release formulation of SDE with a predetermined release period can be prepared by adjusting the BB/oil ratio of the formulation.

Furthermore, it can also be observed from FIG. 3 that when the BB/oil ratio is increased, the release profile of the formulation will be steadier, e.g. delayed onset and insignificant burst release for AF4. The pharmacokinetic parameters are summarized in Table 5. The $T_{max}$ of AF3, AF1 and AF4 are 21 hours, 24 hours and 84 hours, respectively. The $C_{max}$ of AF3, AF1 and AF4 are 87.35 ng/mL, 82.90 ng/mL and 41.1 ng/mL, respectively.

When the BB/oil ratios were about 0.65, about 1, and about 2, the blood concentrations of nalbuphine at 1 hour after administration were about 28.4 ng/mL, about 11.0 ng/mL, and about 6.7 ng/mL, respectively. The results indicate that when the BB/oil ratio is increased, the time to reach an effective blood concentration of nalbuphine may be longer, thus the onset of action of the formulation may be slower.

The following PK parameters support the conclusion that when the BB/oil ratio is increased, the formulation may exhibit a release profile with a longer release period, a lower maximum concentration ($C_{max}$) and a longer time to peak blood concentration level ($T_{max}$), as compared with a formulation having a lower BB/oil ratio.

TABLE 5

Pharmacokinetic parameters after IM injection of AF3, AF1 and AF4 formulations

| Formulation | AF3 | AF1 | AF4 |
|---|---|---|---|
| Injection volume (mL) | 3.2 | 2 | 2 |
| Average BW(kg) | 8.85 | 9.29 | 7.9 |
| Average Dose(mg/kg) | 18.13 | 17.24 | 20.2 |
| $T_{max}$(hr) | 21.00 | 24.00 | 84.0 |
| $C_{max}$(ng/mL) | 87.35 | 82.90 | 41.1 |
| $T_{1/2}$ | 12.69 | 41.14 | 38.99 |
| $AUC_{last}$ (hr*ng/mL) | 4555.63 | 5030.93 | 4075.7 |
| $AUC_{INF\_pred}$ (hr*ng/mL) | 4563.35 | 5577.12 | 4978.4 |

Figure 5:
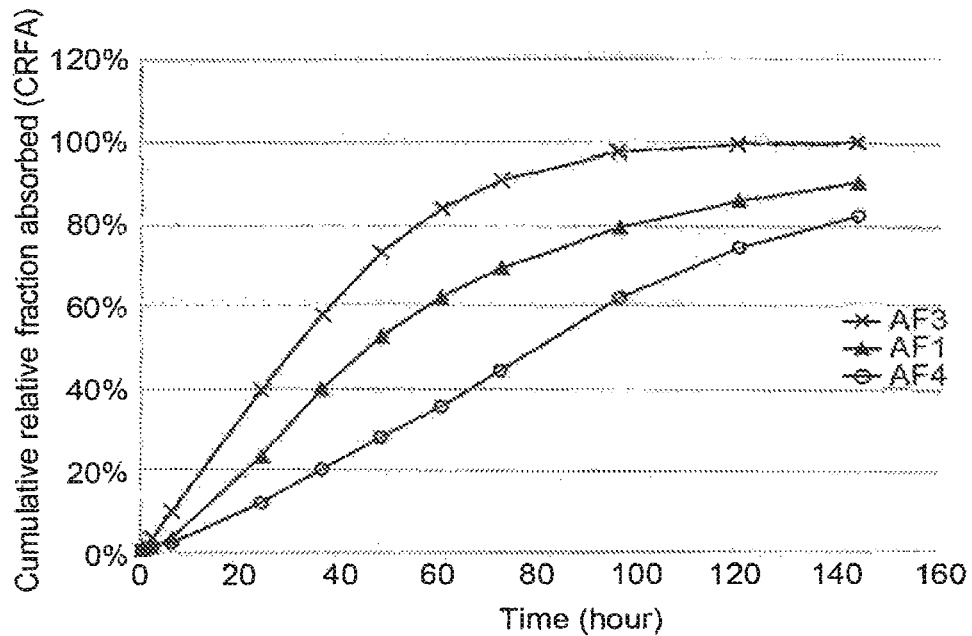
FIG. 5 shows the cumulative relative fraction absorbed (CRFA)-time profiles of nalbuphine in dogs after intramuscular injection of AF3, AF1 and AF4 formulations (total dose: 160 mg/dog).

By using the Wegner-Nelson method, the average plasma concentration versus time curve was transformed into the cumulative relative fraction absorbed (CRFA) versus time curve. Under the assumption that $Ab^\infty$ (total amount of drug absorbed at $t=0\sim\infty$) of each formulation is 100% and the elimination half-life of nalbuphine after i.v. dosing in dogs is about 1.2 hour (Biopharm Drug Dispos. 1985 Octtober-December; 6(4):413-21.), the CRFA versus time curve of each formulation is plotted in FIG. 5. In FIG. 5, when the BB/oil ratio is about 0.65, about 99% of $Ab^\infty$ is absorbed at 144 hours after administration (AF3); when the BB/oil ratio is about 1.18, about 91% of $Ab^\infty$ is absorbed at 144 hours after administration (AF1); when the BB/oil ratio is about 2, about 82% of $Ab^\infty$ is absorbed at 144 hours after administration (AF4). By applying this model, it can be projected that when the BB/oil ratio of the formulation is increased, the relative percentage of $Ab^\infty$ absorbed at the same time point will be lower, which indicates that the formulation with a higher BB/oil ratio may release the dose depot for a longer period of time.

The above experimental results all indicate that the in vitro dissolution profiles of the present formulations are correlated to the in vivo release profiles of the formulations. The in vivo release rate/release period of the present formulation can be controlled or regulated by the BB/oil ratio.

Example 4

In Vitro and In Vivo (on Humans) Studies of Present Formulations (1) Preparation of Present Formulations, by Method B of Example 1

About 600 g of SDE was mixed with about 4025 g of benzyl benzoate. The resulting mixture was stirred at 300 rpm for 60 minutes to give a clear solution. About 3591 g of sesame oil was added into the clear solution, and then stirred at 300 rpm for about 30 minutes. The resulting solution was subjected to filtration sterilization by using Millipore 0.22 μm filters. The final formulation (F8) had an SDE concentration of about 75 mg/mL, and the weight ratio of benzyl benzoate to sesame oil was about 1.12:1 (Table 6).

TABLE 6

F8 formulation

| Sample No. | Benzyl benzoate (w/w %) | Sesame oil (w/w %) | SDE (mg/mL) | BB/oil ratio |
|---|---|---|---|---|
| F8 | 53 | 47 | 75 | 1.12 |

The F8 formulation thus obtained was a homogeneous solution without solid particles, thereby suitable for being sterilized directly by filtration and suitable for large scale production.

(2) In Vitro Dissolution Experiment

Figure 6:
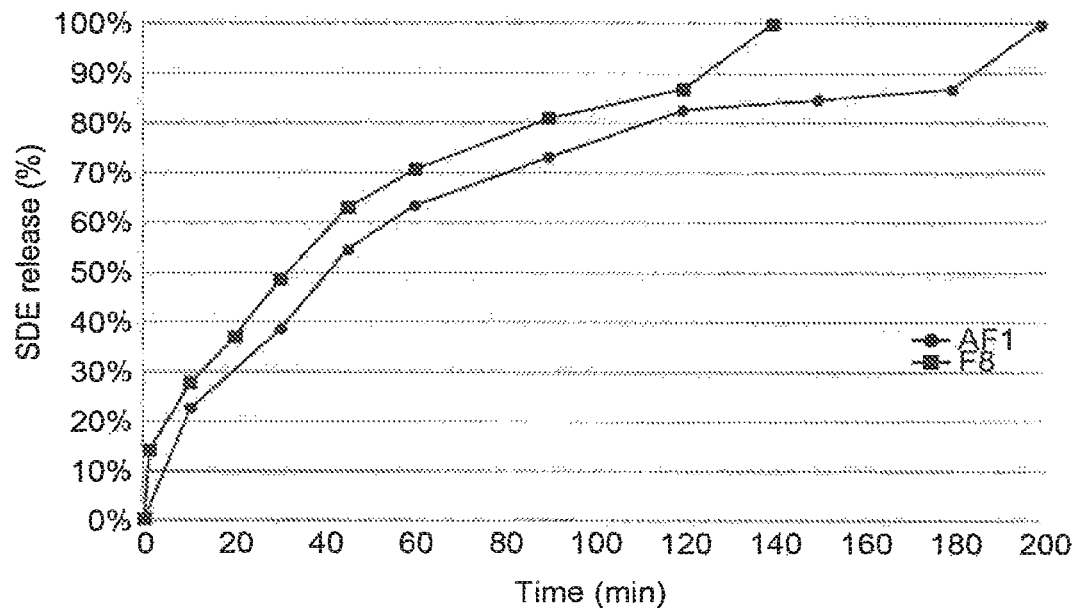
FIG. 6 shows the accumulated dissolution profiles of AF1 and F8 formulations.

In vitro dissolution experiments and UPLC analyses were performed, according to processes disclosed in Example 1, on the F8 formulation. The accumulated SDE dissolution profiles of the F8 formulation and the AF1 formulation are plotted in FIG. 6. It can be seen from FIG. 6 that the dissolution profiles of F8 and AF1 formulations are similar as their BB/oil ratios are similar. When the BB/oil ratio is about 1.1-1.2, the time required for releasing 50% of the total amount of SDE from the formulation into the in vitro medium was about 30-40 minutes.

In view of the duration of action results obtained with AF1 in dogs described above and the similar in vitro dissolution profiles for F8 and AF1, a similar duration of action (i.e. greater than 6 days) with F8 was expected humans.

(3) Phase 1 Clinical Study

A Phase I clinical trial was conducted with the F8 formulation in healthy volunteers. It was designed to evaluate safety and local tolerability and assess the pharmacokinetics of SDE following single dose intramuscular injection. The study enrolled a total of 28 healthy male subjects. All subjects were randomized to 5 cohorts. Cohort 1 (N=4) was treated with single dose Nubain® 17 mg (0.85 mL) via intramuscular injection. Cohorts 2-5 (N=6) were either treated with placebo (N=2) or treated with single dose SDE (N=4) at 75 mg (1 mL), 100 mg (1.33 mL), 125 mg (1.67 mL), and 150 mg (2 mL), respectively. Overall, the escalating doses of SDE up to 150 mg were well tolerated. All adverse events (AEs) were mild. No significant difference was found among the SDE and placebo groups in the number of AEs, the number of subjects with AEs, the severity of AEs, and AE relatedness.

Blood was collected from all 28 subjects who were treated with Nubain®, the F8 formulation, or placebo. Heparinized blood samples were obtained before and at various time points following single dose administration of study medication. Nalbuphine from Nubain® or the F8 formulation were detected and quantitated using the validated LC/MS/MS method. The subsequent analysis of the data involved non-compartmental pharmacokinetics analysis, i.e., $C_{max}$, $T_{max}$, $AUC_{0-t}$, $AUC_{0-inf}$, and $T_{1/2}$. Since SDE is rapidly converted to nalbuphine in the blood, the pharmacokinetic parameters of nalbuphine were calculated using a non-compartment model and actual time vs. plasma concentrations of nalbuphine (Table 7).

The pharmacokinetics of nalbuphine following the administration of the F8 formulation appeared to be dose-proportional. The highest mean $C_{max}$ and $AUC_{0-inf}$ were found at 150 mg SDE and were 9.81 ng/mL and 1353.16 ng*hr/mL, respectively. Plasma nalbuphine reached $C_{max}$ within 45-66 hours ($T_{max}$) after IM administration of 75, 100, 125, and 150 mg SDE.

The average elimination half-life ($T_{1/2}$) of nalbuphine after IM administration of Nubain® (cohort 1) was about 4 h. Following intramuscular injection of the F8 formulation with a total dose ranging from 75 mg to 150 mg, the mean apparent $T_{1/2}$ of nalbuphine ranged from about 56 to 90 hours. The longer apparent half-life was most likely due to slow and prolonged absorption of SDE/nalbuphine from the IM injection site.

TABLE 7

Pharmacokinetic parameters after single IM injection of 17 mg Nubain ® (NH) or escalating doses of F8 formulation.

| Treatment/Dose | | $C_{max}$ (ng/mL) | $T_{max}$ (hr) | $AUC_{0-t}$ (hr*ng/mL) | $AUC_{0-inf}$ (hr*ng/mL) | $T_{1/2}$ (hr) |
|---|---|---|---|---|---|---|
| NH 17 mg | Mean | 85.73 | 0.25 | 171.74 | 174.16 | 4.06 |
|  | SD | 18.61 | 0 | 15.99 | 15.53 | 1.13 |
| SDE 75 mg | Mean | 5.45 | 66 | 647.84 | 692.27 | 55.75 |
|  | SD | 0.85 | 22.98 | 96.95 | 114.00 | 5.54 |
| SDE 100 mg | Mean | 5.65 | 66 | 811.34 | 936.17 | 85.45 |
|  | SD | 1.50 | 40.99 | 145.69 | 176.27 | 29.70 |
| SDE 125 mg | Mean | 7.31 | 45 | 1047.45 | 1219.71 | 89.83 |
|  | SD | 1.79 | 24.74 | 205.77 | 263.16 | 24.74 |
| SDE 150 mg | Mean | 9.81 | 60 | 1214.98 | 1353.16 | 73.4 |
|  | SD | 2.94 | 13.86 | 155.93 | 137.55 | 30.74 |

Figure 7:
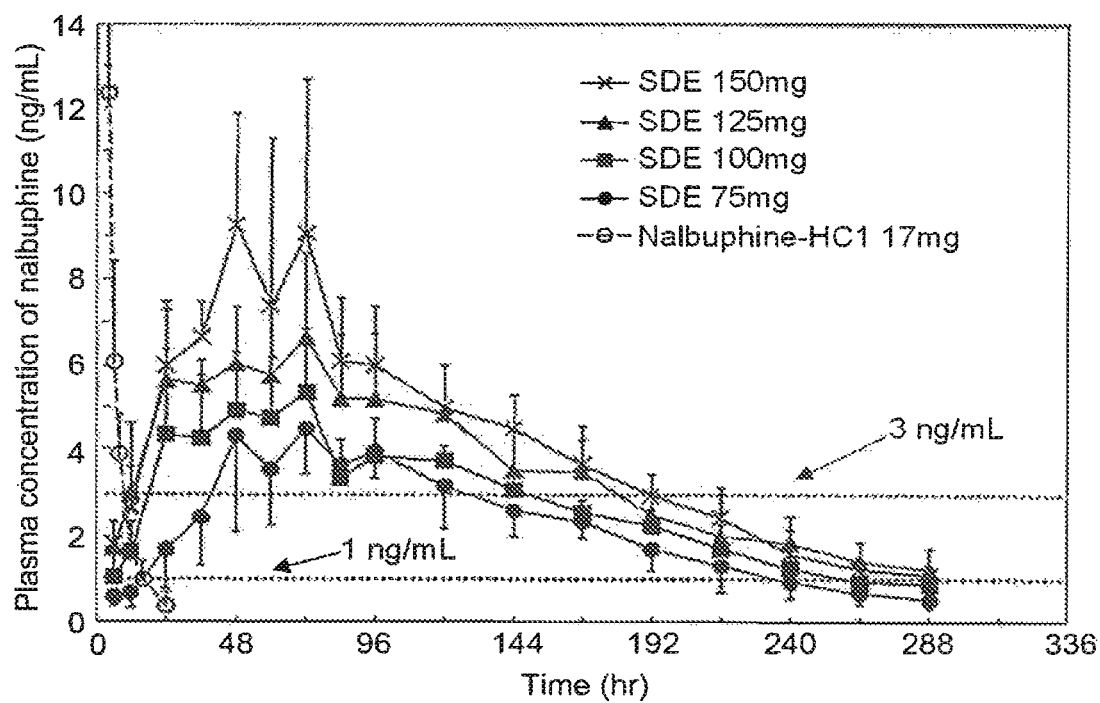
FIG. 7 shows the mean plasma concentration-time profile of nalbuphine after human subjects received a single intramuscular injection of 17 mg Nubain® (Nalbuphine-HCl) or escalating doses (75, 100, 125, and 150 mg) of the F8 formulation.

FIG. 7 shows the plasma concentrations of nalbuphine following administration of various dose of the F8 formulation and of one dose of Nubain®. The plasma concentrations of nalbuphine were above 1 ng/mL or 3 ng/mL for at least 220 or 120 hours, respectively, in all 16 subjects receiving 75-150 mg SDE in the F8 formulation. However, following intramuscular injection of Nubain® 17 mg, the plasma concentrations of nalbuphine remained above 1 ng/mL or 3 ng/mL for only 16 or 8 hours, respectively. Under the assumption that the effective plasma concentration of nalbuphine for analgesia in moderate to severe pain is greater than 1 ng/mL, more preferably greater than 3 ng/mL (Can J Anaesth. 1991 March; 38(2):175-82; European Journal of Clinical Pharmacology 1987, Volume 33, Issue 3, pp 297-301), the duration of action of a single injection of the F8 formulation would be much longer than that covered by a single injection of Nubain®. In the cohort receiving 125 mg SDE, the mean plasma concentration of nalbuphine was above 3 ng/mL between 12 to 168 hours of dosing, which indicated that the duration of action was about 6.5 days (168−12=156 hours=6.5 days). In the cohort receiving 150 mg SDE, the mean plasma concentration of nalbuphine was above 3 ng/mL between 24 to 168 hours of dosing, and was above 1 ng/mL between 6 to 288 hours of dosing, which indicated that the duration of action was about 6-12 days (168−24=144 hours=b6 days; 288−6=282 hours=11.75 days). For some individuals, the plasma concentrations of nalbuphine were above 3 ng/mL between 12 to 216 hours of dosing, which indicated that the duration of action was about 8.5 days (216−12=204 hours=8.5 days). This indicates that the F8 formulation may be administered to a patient at 6 to 36 hours prior to the onset of pain symptoms. For example, the onset of pain symptoms is during or after a surgical operation. Accordingly, the F8 formulation may be administered to a patient at 6 to 36 hours prior to a surgical operation, and may effectively relieve pain during and immediately after the surgical operation. For example, the F8 formulation may be administered at 12-36 hours or 12-24 hours prior to the surgical operation.

(4) Bioavailability Study

A bioavailability study with the F8 formulation and Bain® (Nalbuphine HCl IM injection) was conducted on healthy volunteers. A total of twelve subjects completed the crossover study. Each subject received a single dose of reference drug (Bain®, Nalbuphine HCl IM injection, 10 mg/mL×2 mL) in period I and the F8 formulation (SDE IM injection, 75 mg/mL×2 mL) in period II. There was a minimum 5-day washout period between period I and period II. In period I, the blood samples were drawn prior to the dosing, and 0.083, 0.25, 0.5, 1, 1.5, 2, 3, 4, 6, 8, 12, and 24 hours after dosing. In period II, the blood samples were drawn prior to the dosing, and 6, 12, 24, 48, 60, 72, 96, 120, 168, 216, 288 and 360 hours after dosing.

The whole blood concentrations of nalbuphine in the samples were determined by LC-MS/MS. $AUC_{0-t}$, $AUC_{0-inf}$, $C_{max}$, $T_{max}$, $T_{1/2}$, and MRT for nalbuphine in whole blood were determined by non-compartment methods. In addition, relative bioavailability of SDE compared to Nalbuphine (Bain®) was calculated.

No serious adverse events occurred during this study. Pharmacokinetic parameters of nalbuphine for Bain® and the F8 formulation are presented as mean±the standard deviation (SD) in Table 8.

TABLE 8

Pharmacokinetic parameters of nalbuphine for Nalbuphine (Bain ®) and the F8 formulation.

| Treatment/Dose | | $AUC_{0-t}$ (ng/mL*h) | $AUC_{0-inf}$ (ng/mL*h) | $C_{max}$ (ng/mL) | $T_{max}$ (h) | MRT (h) | $T_{1/2}$ (h) |
|---|---|---|---|---|---|---|---|
| Bain ® 20 mg | Mean | 319.3 | 323.0 | 115.45 | 0.40 | 4.15 | 4.03 |
|  | SD | 85.3 | 86.5 | 56.45 | 0.13 | 0.61 | 0.54 |
| SDE 150 mg | Mean | 1687.4 | 1832.0 | 15.40 | 64.00 | 149.38 | 83.16 |
|  | SD | 385.6 | 402.2 | 6.42 | 9.34 | 69.07 | 46.45 |

Figure 8:
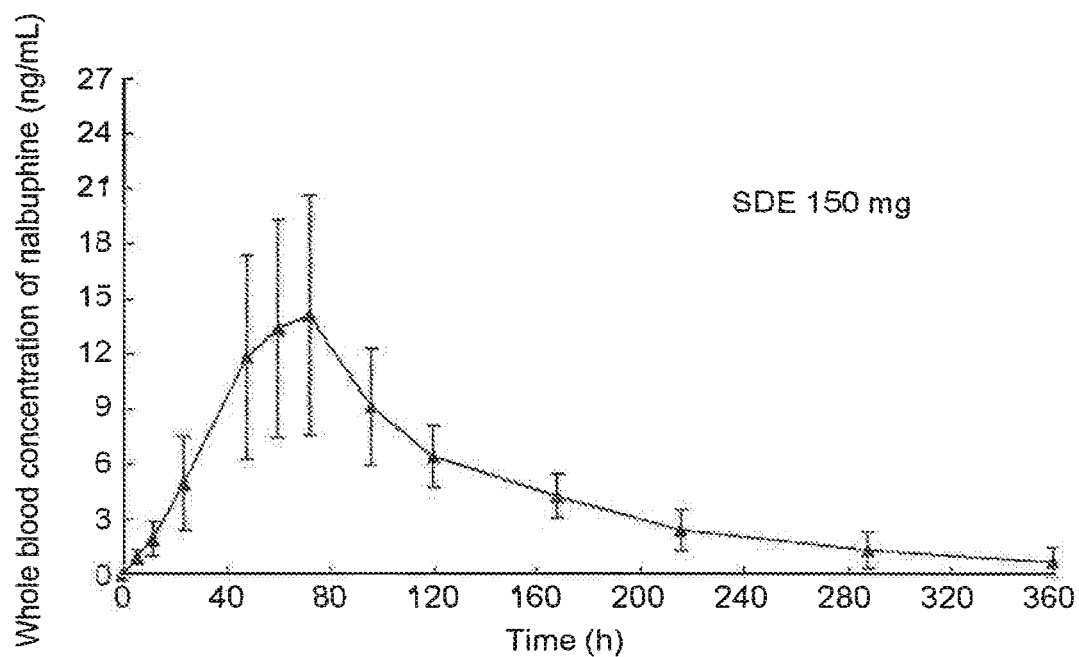
FIG. 8 shows the mean whole blood concentration-time profile of nalbuphine after human subjects received a single intramuscular injection of the F8 formulation (total dose: 150 mg/person).

FIG. 8 shows the mean whole blood concentration-time profiles of nalbuphine after subjects received the F8 formulation from 0 to 360 hours of dosing in period II described above. In this bioavailability study, the mean whole blood concentration of nalbuphine was above 3 ng/mL between 24 to 168 hours of dosing, which indicated that the duration of action was about 6 days (Table 9). The result is consistent with the finding in the cohort receiving 150 mg SDE of Phase 1 study (plasma concentration of nalbuphine). For some individuals, the whole blood concentrations of nalbuphine were above 3 ng/mL between 12 to 216 hours of dosing, which indicated that the duration of action was about 8.5 days. In addition, the mean whole blood concentration of nalbuphine was above 1 ng/mL between 6 to 288 hours of dosing, which indicated that the duration of action was about 12 days.

TABLE 9

Mean whole blood concentration-time data of nalbuphine for the F8 formulation

| Time (h) | Mean (ng/mL) | SD |
|---|---|---|
| 0 | — | — |
| 6 | 1.09 | 0.39 |
| 12 | 2.04 | 0.94 |
| 24 | 5.03 | 2.55 |
| 48 | 11.83 | 5.51 |
| 60 | 13.39 | 5.87 |
| 72 | 14.12 | 6.49 |
| 96 | 9.17 | 3.15 |
| 120 | 6.48 | 1.67 |
| 168 | 4.33 | 1.19 |
| 216 | 2.51 | 1.10 |
| 288 | 1.44 | 0.98 |
| 360 | 0.81 | 0.78 |

The relative bioavailability (F) of nalbuphine from the F8 formulation to nalbuphine from Bain® was about 86.2±12.1 (%). In addition, the mean absorption time (MAT) and absorption rate (Ka) of nalbuphine from the F8 formulation were about 145.2±69.1 hour and about 0.0081±0.0030 h$^{-1}$, respectively. The bioavailability study shows that the duration of action of the present formulation may be equal to or greater than 6 days when the BB/oil ratio is set to about 1.12. On some individuals, the duration of action of the present formulation may be about 5 days.

By correlating the dog study results (Example 3) with the human study results, it can be concluded that when the formulation having a BB/oil ratio of less than 1, e.g., about 0.65, is administered to a human subject via IM injection, the duration of action of the formulation may be less than 6 days; while when the formulation having a BB/oil ratio of more than 1, e.g., about 2, is administered to a human subject via IM injection, the duration of action of the formulation may be greater than 6 days. Accordingly, the present invention may provide extended release formulations of SDE with various release periods by adjusting the BB/oil ratio. For example, when a longer duration of action is intended (e.g. 1 or 2 weeks, or longer), the BB/oil ratio may be set to about 1 or greater than 1, for example, 2 or 3; and when a shorter duration of action is intended (e.g. 3 or 4 days), the BB/oil ratio may be set to less than 1, for example, 0.5 or 0.65.

The primary efficacy endpoint was pain assessment calculated as the area under the curve of VAS pain intensity scores through 48 hours after surgery. The secondary efficacy endpoints included pain assessment measured with VAS; time from the end of operation to the first rescue medication dosing; the consumption of oral ketorolac. Pain intensity was assessed right before the first use of PCA ketorolac, and at 1±0.1, 2±0.1, 3±0.1, 4±0.25, 8±0.5, 12±0.5, 16±0.5, 20±0.5, 24±1, 28±1, 32±2, 36±2, 40±2, 44±2, 48±2 hours after the surgery, and was assessed during Days 3-7 in the morning and evening, as well as during special events such as bowel movements.

For the calculation of AUC, data were imputed with the use of the windowed worst observation carried forward plus last observation carried forward method. For subjects who used rescue medication for pain relief, their VAS scores recorded within the window of ketorolac medication (6 hours, which is one half-life of ketorolac) were replaced by the "worst" observation (i.e., the highest score before taking ketorolac), hereafter called "adjusted VAS scores."

The $AUC_{0-24}$ and $AUC_{0-48}$ of the mean adjusted VAS scores of SDE and placebo groups were calculated by using the trapezoidal method and summarized in Table 10.

TABLE 10

Statistical analysis of $AUC_{0-24}$ and $AUC_{0-48}$ by treatment after hemorrhoid operation.

| Population | Mean ± SD | | SDE - Placebo | |
| --- | --- | --- | --- | --- |
| | SDE | Placebo | LS-mean [95% CI][1] | p-value[2] |
| mITT | | | | |
| N | 103 | 106 | | |
| $AUC_{0-24}$ | 109.42 ± 55.04 | 126.71 ± 49.22 | −16.86 [−31.05; −2.67] | 0.0201* |
| $AUC_{0-48}$ | 209.93 ± 111.26 | 253.53 ± 108.49 | −42.20 [−71,68; −12.71] | 0.0052* |

*mITT population: modified Intention-To-Treat population (5) Phase 2/3 Clinical Study A random, placebo-controlled, single dose, parallel design, phase 2/3 study was conducted with 209 male and female patients to assess the safety and efficacy of the intramuscular injection of F8 formulation in the treatment of postoperative pain following hemorrhoidectomy.

The subjects were divided into two groups, of which Group 1 (n=103) was treated with a single dose of intramuscular SDE 150 mg (2 mL), and Group 2 (n=106) was treated with a single dose of intramuscular placebo (2 mL). All subjects were given a single dose of SDE or placebo via intramuscular injection 24±12 hours before hemorrhoid surgery. The subjects were allowed to take rescue medication and monitored for 7 days after dosing. Statistical analyses were performed on the data to compare the two groups.

Figure 9:
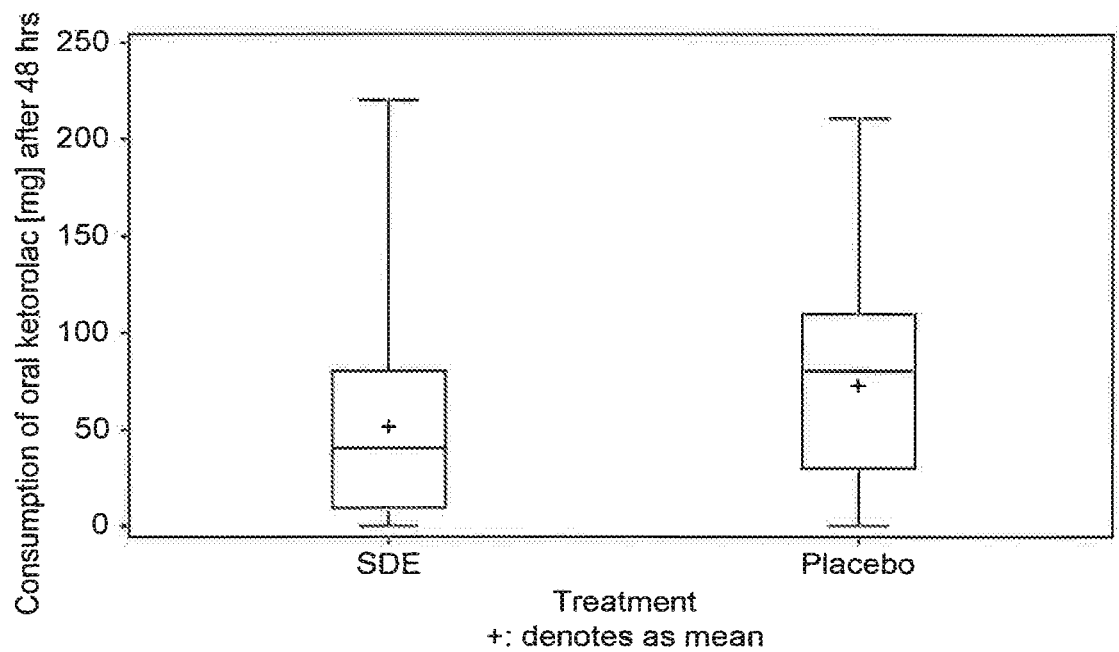
FIG. 9 shows the distribution statistics of the consumption of oral ketorolac through 48 hours after hemorrhoid operation on subjects who received SDE prior to surgery or on subjects who received placebo prior to surgery.

The $AUC_{0-48}$ of the SDE group showed statistically significant superiority against placebo group in mITT population (209.93±111.26 vs. 253.53±108.49, p=0.0052). The distribution statistics for the amount of oral ketorolac consumption after 48 hours post-operation by treatment was graphed as the box plot presented in FIG. 9. Both the mean and median consumption of oral ketorolac were lower in SDE group (Mean: 51.36 mg, Median: 40.00 mg) than those in the placebo group (Mean: 73.30 mg, Median: 80.00 mg).

Furthermore, the time of the first use of post-surgical analgesic from post-operation was assessed and the results of distribution statistics are summarized in Table 11. Longer periods of time for the first use of post-operational analgesic in SDE groups were observed. The mean time period of SDE group (12.57 hours) was prolonged, compared to that of the placebo group (4.93 hours).

TABLE 11

Distribution statistics of time (hour) for the first use of post-operational analgesic by treatment

| Population | SDE | Placebo | Overall |
| --- | --- | --- | --- |
| mITT (N) | 103 | 106 | 209 |
| NObs[1] | 87 | 99 | 186 |
| Mean (SD) | 12.57 (1.68) | 4.93 (0.47) | 9.68 (1.01) |
| Q1 [95% CI][2] | 2.27 [1.32; 2.78] | 1.43 [0.98; 1.90] | 1.80 [1.23; 2.22] |
| Median [95% CI][2, 3] | 4.42 [3.47; 5.80] | 3.28 [2.33; 4.73] | 4.23 [3.03; 4.75] |
| Q3 [95% CI][2] | 11.25 [8.33; 45.65] | 6.52 [5.67; 7.60] | 7.95 [6.60; 10.63] |

In summary, the trends of VAS scores for pain intensity measured over time through 48 hours post-operation, the time from the end of operation to the first rescue medication dosing and the consumption of oral ketorolac within 48 hours were consistent. All these clinical results indicated that the F8 formulation may be administered to a patient prior to a hemorrhoid operation, and may effectively relieve pain immediately after the hemorrhoid operation.

Figure 10:
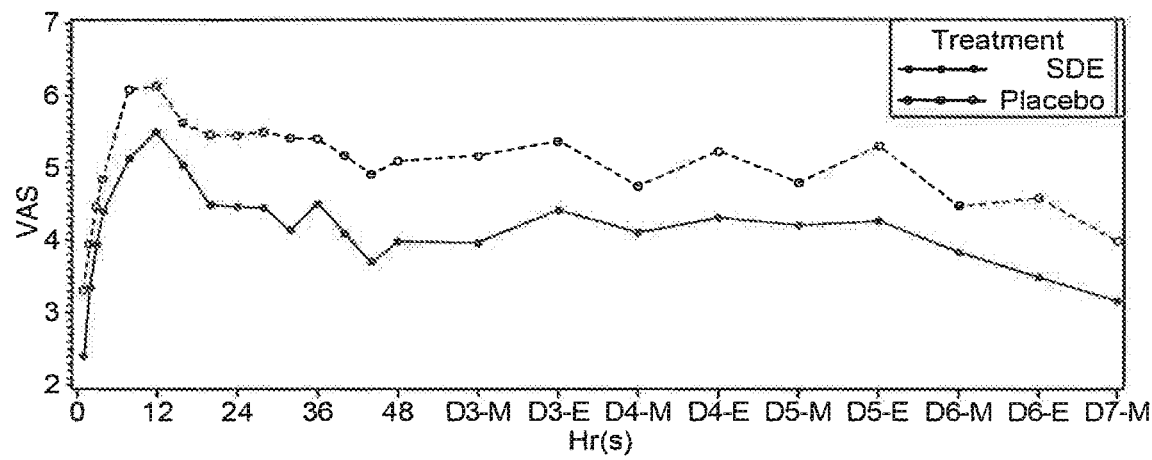
FIG. 10 shows the plot of adjusted VAS scores over time through 0 hr to 7 days after hemorrhoid operation of mITT population.

FIG. 10 shows the plot of adjusted VAS scores over time through 0 hr to 7 days after hemorrhoid operation of mITT population. The adjusted $AUC_{0\text{-}final}$ of the mean VAS scores for SDE and placebo groups were calculated by using the trapezoidal method and summarized in Table 12. The $AUC_{0\text{-}final}$ of mean adjusted VAS scores of pain intensity of the SDE group showed statistically significant superiority against the placebo group in mITT population (630.79±350.90 vs. 749.94±353.72, p=0.0165). In addition, the adjusted VAS score of pain intensity in the SDE group was lower at beginning of the assessment measured the first 1 hour and at Day 7 morning after hemorrhoid operation (see the first and the last data point of FIG. 10). The adjusted VAS score of the SDE group was lower than the placebo group throughout the 7 days after the hemorrhoid operation. Accordingly, the F8 formulation may be administered to a patient prior to a hemorrhoid operation, and may effectively relieve pain immediately after the hemorrhoid operation with the duration of action persisting for at least about 5 or 6 days.

TABLE 12

Statistical analysis of $AUC_{0\text{-}final}$ (based on adjusted VAS scores) by treatment after hemorrhoid operation

| Population | Mean ± SD | | SDE - Placebo | |
| --- | --- | --- | --- | --- |
| | SDE | Placebo | LS-mean [95% CI][1] | p-value[2] |
| mITT | | | | |
| N | 103 | 106 | | |
| $AUC_{0\text{-}final}$ | 630.79 ± 350.90 | 749.94 ± 353.72 | −115.20 [−209.153; −21.26] | 0.0165* |

Example 5

Stability Data of the Present Formulation

The F8 formulation prepared according to Example 4 was stored at 2-8° C. for 24 months. The formulation remained as a clear and lightly yellow oily solution for the whole period of 24 months. In the meantime, the formulation was tested periodically by HPLC to determine its Assay (Table 13).

TABLE 13

Assay of the F8 formulation at 2-8° C. for 24 months.

| Time of sampling (month) | Assay by HPLC (% of target) |
| --- | --- |
| 0 | 104.3% |
| 6 | 105.2% |
| 12 | 101.7% |
| 18 | 101.7% |
| 24 | 101.3% |

It can be seen from Table 13 that the F8 formulation is stable for storage at 2-8° C. for at least 24 months. The freeze-thaw test conducted in Example 2 also demonstrates that the formulation of the present invention can remain homogeneous at about 0-4° C. while not forming precipitates or solid particles when being returned to room temperature. The stability testing results indicate that the formulation, having a SDE concentration (about 75 mg/mL) higher than the original solubility/saturated concentration (about 60 mg/mL), prepared by Method B can exhibit superior stability to satisfy commercial needs, e.g. long shelf-life under low-temperature storage.

In another example, the F8 formulation was respectively stored at 5, 25 and 40° C. for 6 months. Samples collected from each group were tested periodically by HPLC to determine the formation of degradation products (Table 14).

TABLE 14

Stability of the F8 formulation at 5, 25, and 40° C. for 6 months

| Time of sampling (month) | Total impurities by HPLC | | |
| --- | --- | --- | --- |
| | Stored at 5° C. | Stored at 25° C. | Stored at 40° C. |
| 0 | 0.37% | 0.37% | 0.37% |
| 1 | 0.42% | 0.45% | 0.47% |
| 3 | 0.39% | 0.50% | 0.85% |
| 6 | 0.38% | 0.65% | 1.66% |

It can be seen from Table 14 that when stored at 25° C. or 40° C., the F8 formulation generated more impurities. This indicates that the formulation is more suitable to be stored at a temperature lower than room temperature. Since the formulation of the present invention can remain homogeneous and stable at 2-8° C. while not forming solid particles when returned to room temperature, its shelf-life can be further prolonged by being stored at a lower temperature.

Example 6

Improvement of SDE Solubility in Various Solvent Systems Containing Different Alkyl Alcohols as the Solubilizing Agent (1) Solubility Test of SDE Solutions Table 15 shows the compositions of the tested solvent systems by weight/weight percent (w/w %). The solvent systems each comprise sesame oil, benzyl benzoate and different alkyl alcohols (i.e., ethanol, 1-propanol, 2-propanol, 1-butanol and t-butanol).

Each of the solvent systems was prepared by mixing each component with the exact volume (μl) corresponding to the w/w % listed in Table 15. About 500 μl of each of the solvent systems was prepared and was vortexed for 3 minutes or more to fully mix each component. An appropriate amount of SDE was added into 250 μl of each of the solvent systems and the resulting mixtures were sonicated for 10 minutes. If the previously added SDE was completely dissolved, an additional 4-8 mg of SDE was added into the mixture and which was then sonicated for another 10 minutes. The step of adding 4-8 mg of SDE was repeated until the mixture was saturated to show undissolved SDE precipitates. All of the mixtures were sonicated for at least 30 minutes, and then centrifuged to collect the supernatants. The supernatants were treated with acetonitrile and then subjected to UPLC analysis.

(2) UPLC Analysis

The SDE concentrations in the supernatants collected from samples S1-S8 were respectively determined by UPLC according to the method of Example 1, except that the run time was 15 minutes and the sample volume was 1 ul.

The saturated SDE concentrations (i.e., solubility) for each tested solvent systems are shown in Table 15. It is seen that the addition of alkyl alcohols in the solvent systems can significantly increase the SDE solubility, although the solubility of SDE in each of the alcohols alone is rather low. The solubility of SDE in ethanol, 1-propanol, or t-butanol is about 10-30 mg/mL (Table 16).

The solubility of SDE in the solvent systems may be increased by at least 30% when there is 10% of alkyl alcohol added.

TABLE 15

Effect of alkyl alcohol on increasing SDE solubility in the present formulations

| No. | alcohol type | Composition of the solvent system (w/w %) | | | SDE Solubility (mg/mL) | Solubility Improvement |
|---|---|---|---|---|---|---|
| | | alcohol | sesame oil | benzyl benzoate | | |
| S1 | NC* | 0 | 40 | 60 | 159.8 | — |
| S2 | Ethanol | 10 | 40 | 50 | 267.7 | 168% |
| S3 | 1-Propanol | 10 | 40 | 50 | 254.1 | 159% |
| S4 | 2-Propanol | 10 | 40 | 50 | 235.2 | 147% |
| S5 | 1-Butanol | 10 | 40 | 50 | 222.0 | 139% |
| S6 | tert-Butanol | 10 | 40 | 50 | 211.2 | 132% |

*NC: Negative control, i.e. no alcohol is added.

TABLE 16

The solubility of SDE in various solvents

| Sample No. | Solvent | Solubility of SDE in the solvent (mg/mL) |
|---|---|---|
| 1 | Benzyl benzoate (BB) | 373.44 |
| 2 | Benzyl alcohol | 583.13 |
| 4 | Ethanol | 15.86 |
| 5 | 1-Propanol | 32.46 |
| 6 | t-Butanol | 19.46 |
| 11 | Sesame oil | 5.93 |

Example 7

Solubility of SDE in Solvent Systems Comprising Different Types and Amounts of Alkyl Alcohols Five groups of solvent systems containing 40% by weight of sesame oil were respectively prepared according to the method of Example 6 by using the compositions as listed in Table 17; and among them, five different alcohols (i.e., ethanol, 1-propanol, 2-propanol, 1-butanol, and tert-butanol) were used in the five groups. SDE was dissolved in each of the solvent systems till saturation by following the method of Example 6. The SDE concentrations in the supernatants collected from each of the samples (i.e. the saturated SDE concentration, or SDE solubility) were respectively determined by UPLC using the method of Example 6.

TABLE 17

Solvent systems with various types and amounts of alcohols
Components of the solvent system (w/w %)

| Sesame oil | Alcohol * | Benzyl benzoate |
|---|---|---|
| 40 | 0 | 60 |
| 40 | 2.5 | 57.5 |
| 40 | 5 | 55 |
| 40 | 10 | 50 |
| 40 | 20 | 40 |
| 40 | 30 | 30 |
| 40 | 40 | 20 |

* Ethanol, 1-propanol, 2-propanol, 1-butanol, and tert-butanol were used in the five groups, respectively.

Figure 11:
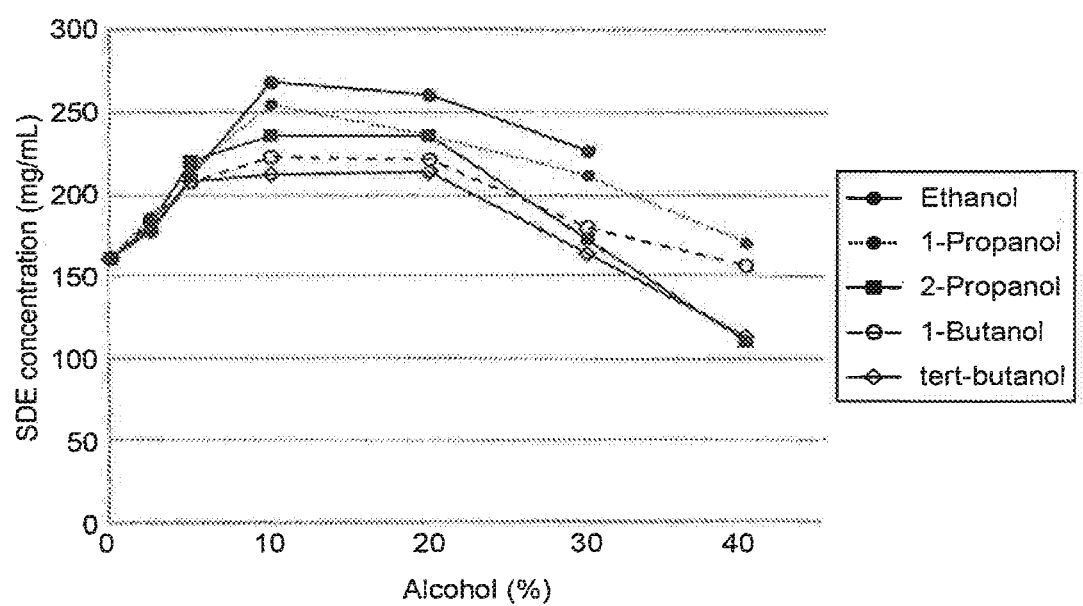
FIG. 11 shows the saturated concentration/solubility of SDE in different solvent systems containing different alkyl alcohols.

The UPLC analysis results are divided into the five groups to illustrate the effect of changing the alcohol on the SDE solubility, as depicted in FIG. 11. It can be seen from FIG. 11 that when ethanol is replaced by 1-propanol, 2-propanol, 1-butanol, or tert-butanol, the trends of solubility improvement observed are similar. For C2-C4 alcohols, when 2.5-30% by weight of the alcohol is added into the solvent system, the solubility of SDE can be significantly increased; and when about 10-20% by weight of the alcohol is added into the solvent system, the SDE solubility can be maximized.

Example 8

In Vitro Release Study of Present Formulations Containing Various Alkyl Alcohols (1) Preparation of Present Formulations Five present formulations were prepared according to Method A of Example 1 (i.e., mixing the alkyl alcohol, BB and oil, then adding SDE) by using various solvent systems as listed in Tables 18. The solubility of SDE in formulations comprising an oli-miscible retaining solvent and a pharmaceutically acceptable oil may be significantly increased by adding an alkyl alcohol. As such, Method A is sufficient to prepare a homogenous alcohol-containing formulation having a SDE concentration that is greater than the SDE solubility of the formulation without the alcohol, as long as the intended concentration of SDE in the alcohol-containing formulation is lower than the saturated concentration.

For the five formulations listed in Table 18, each formulation contains 10% ethanol and the BB/oil ratio ranges from 0.5 to 16.

TABLE 18

The present formulations with ethanol, at various BB/oil ratios

| Sample No. | Ethanol (w/w %) | Benzyl benzoate (w/w %) | Sesame oil (w/w %) | SDE (mg/mL) | BB/oil ratio |
|---|---|---|---|---|---|
| N1 | 10 | 30 | 60 | 75 | 0.5 |
| N2 | 10 | 45 | 45 | 150 | 1 |
| N3 | 10 | 67.5 | 22.5 | 150 | 3 |

TABLE 18-continued

The present formulations with ethanol, at various BB/oil ratios

| Sample No. | Ethanol (w/w %) | Benzyl benzoate (w/w %) | Sesame oil (w/w %) | SDE (mg/mL) | BB/oil ratio |
|---|---|---|---|---|---|
| N4 | 10 | 80 | 10 | 150 | 8 |
| N5 | 10 | 85 | 5 | 150 | 16 |

(2) In Vitro Dissolution Experiment

In vitro dissolution experiments and UPLC analyses were performed according to the method of Example 1. The accumulated SDE dissolution profiles of the five formulations listed in Tables 18 are plotted in FIG. 12.

Figure 12:
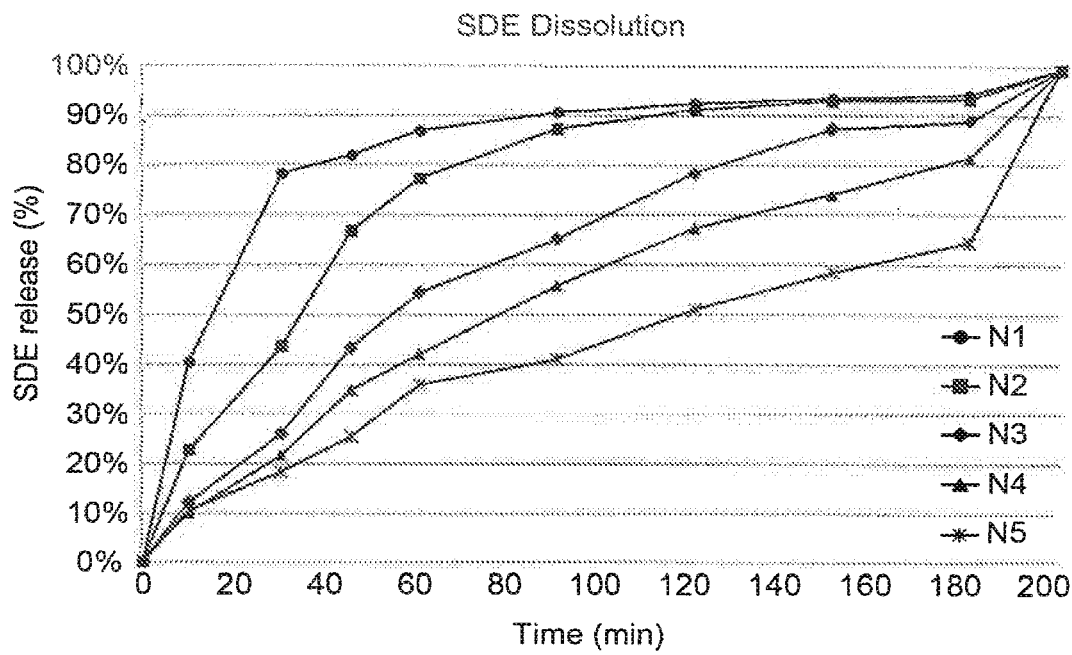
FIG. 12 shows the accumulated dissolution profiles of N1-N5 formulations.

In FIG. 12, it can be seen that the trend observed in FIG. 1 remains when ethanol is added into the formulations (N1-N5 of Table 18).

The presence or absence of an alkyl alcohol in the present formulation does not significantly affect the correlation between the dissolution/release rate and the BB/oil ratio, though the addition of the alcohol can significantly improve the solubility of SDE in the formulation so as to give a homogeneous formulation having a SDE concentration higher than that possible for the formulation without the alcohol.

Example 9

In Vitro Release Study of Present Formulations with or without Alkyl Alcohol (1) Preparation of Formulations Six formulations were prepared using various solvent systems as listed in Tables 19-20. Among them, formulations F8 and AF1 were prepared according Method B of Example 1, and the remaining formulations were prepared according to Method A of Example 1 (i.e. mixing the alkyl alcohol, BB and oil, then adding SDE).

For the three formulations listed in Table 19, the BB/oil ratios are all 16. For the N5 and N10 formulations, ethanol and 1-butanol were respectively added in the formulations. For the N7 formulation, there was no alcohol used in the formulation.

For the three formulations listed in Table 20, the BB/oil ratios are all about 1. For the N2 formulation, ethanol was added in the formulation; and for the F8 and AF1 formulations, there were no alcohol used in the formulations.

TABLE 19

The present formulations with/without alcohols, at the BB/oil ratio of 16

| | Components of the solvent system (w/w %) | | | | |
|---|---|---|---|---|---|
| Sample No. | Alcohol type | Alcohol | Benzyl benzoate | Sesame oil | SDE (mg/mL) | BB/oil ratio |
| N7 | | 0 | 94 | 6 | 150 | 16 |
| N5 | Ethanol | 10 | 85 | 5 | 150 | 16 |
| N10 | 1-butanol | 10 | 85 | 5 | 150 | 16 |

TABLE 20

The present formulations with/without alcohols, at the BB/oil ratio of about 1

| | Components of the solvent system (w/w %) | | | | |
|---|---|---|---|---|---|
| Sample No. | Ethanol | Benzyl benzoate | Sesame oil | SDE (mg/mL) | BB/oil ratio |
| F8 | 0 | 53 | 47 | 75 | 1.12 |
| AF1 | 0 | 54.2 | 45.8 | 80 | 1.18 |
| N2 | 10 | 45 | 45 | 150 | 1 |

(2) In Vitro Dissolution Experiment

Figure 13:
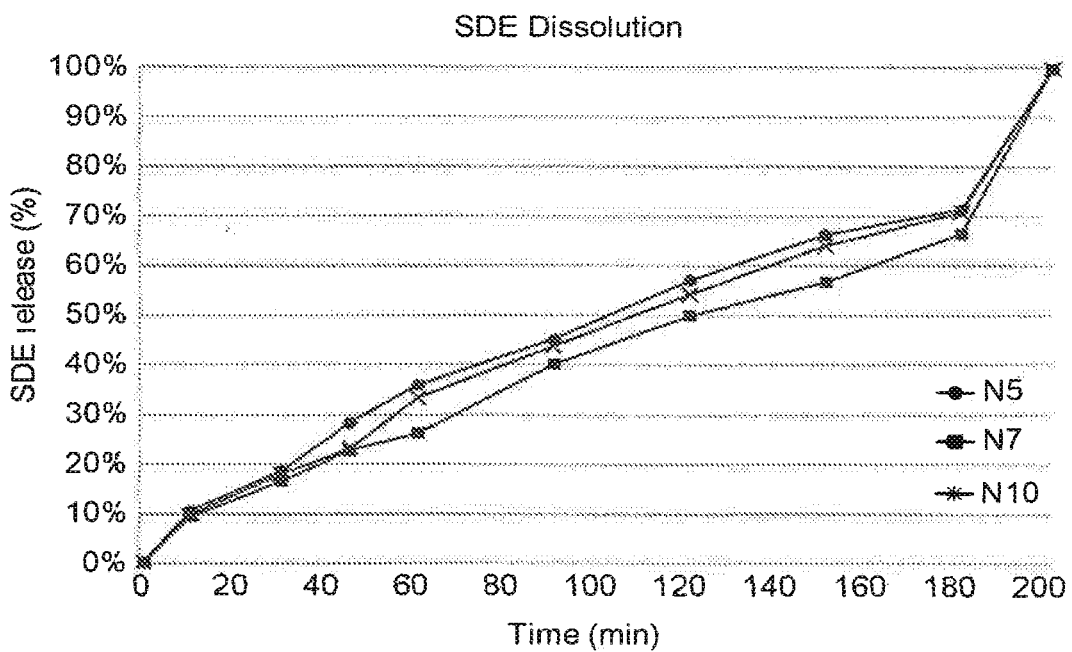
FIG. 13 shows the accumulated dissolution profiles of N5, N7 and N10 formulations.
Figure 14:
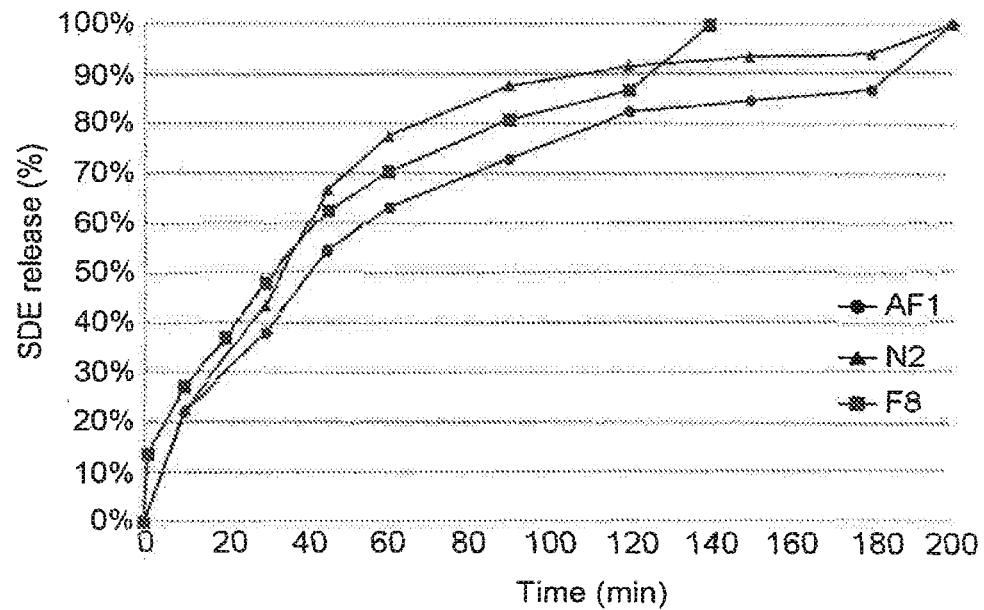
FIG. 14 shows the accumulated dissolution profiles of AF1, N2, and F8 formulations.

In vitro dissolution experiments and UPLC analyses were performed, according to the method of Example 1, on the formulations listed in Tables 19-20. The accumulated SDE dissolution profiles of the eight formulations of Tables 19 and 20 are plotted in FIGS. 13-14, respectively. As shown in FIGS. 13-14, the presence or absence of an alkyl alcohol, does not significantly affect the dissolution rate of SDE from the formulation as long as the BB/oil ratio remains the same or similar. When the BB/oil ratio is set to about 16, the times required for releasing 50% of the total amount of SDE from the four formulations into the in vitro medium are all about 100-120 minutes (N7, N5 and N10 of Table 19). When the BB/oil ratio is set to about 1, the times required for releasing 50% of the total amount of SDE from the three formulations into the in vitro medium are all about 20-50 minutes (F8, AF1, and N2 of Table 20).

The results show that the presence or absence of an alkyl alcohol does not significantly affect the dissolution/release rate of the present formulations as long as the BB/oil ratio remains the same or similar.

Example 10

In Vitro Release Study of Formulations Containing Different Oils (1) Preparation of Formulations Four formulations were prepared according to Method A of Example 1 by using different solvent systems as listed in Table 21 (i.e., mixing ethanol, BB and the oil, then adding SDE). For the N2 and N14 formulations, the BB/oil ratios are about 1; while for the N4 and N13 formulations, the BB/oil ratios are about 8. In the N2 and N4 formulation, the oil used is sesame oil; and in the N14 and N13 formulation, the oil used is castor oil.

TABLE 21

The formulations with different oils

| | Components of the solvent system (w/w %) | | | | | |
|---|---|---|---|---|---|---|
| Sample No. | Oil Type | Oil | Ethanol | Benzyl benzoate | SDE (mg/mL) | BB/oil ratio |
| N2 | sesame oil | 45 | 10 | 45 | 150 | 1 |
| N14 | castor oil | 45 | 10 | 45 | 150 | 1 |
| N4 | sesame oil | 10 | 10 | 80 | 150 | 8 |
| N13 | castor oil | 10 | 10 | 80 | 150 | 8 |

(2) In Vitro Dissolution Experiment

In vitro dissolution experiments and UPLC analyses were performed, according to the method in Example 1, on the four formulations. The accumulated SDE dissolution profiles of the four formulations are plotted in FIG. 15.

Figure 15:
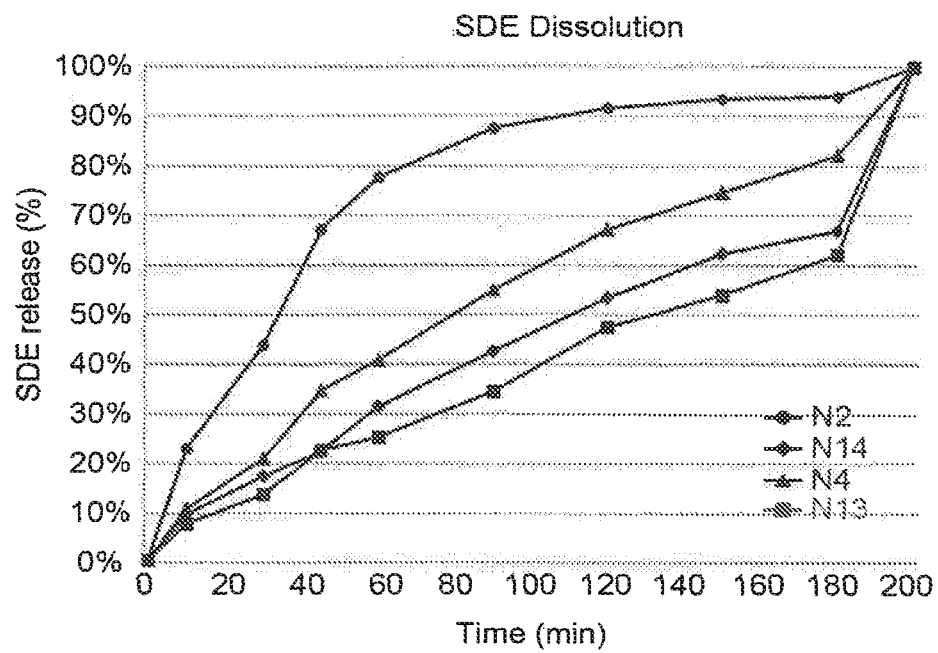
FIG. 15 shows the accumulated dissolution profiles of N2, N4, N13, and N14 formulations.

As shown in FIG. 15, when the oil used is sesame oil and the BB/oil ratio is set to 1, the time required for releasing about 50% of the total amount of SDE from the formulation into the in vitro medium is about 30-40 minutes (N2); and when the oil used is castor oil and the BB/oil ratio is set to 1, the time required for releasing 50% of the total amount of SDE from the formulation into the in vitro medium is about 100-120 minutes (N14). On the other hand, when the oil used is sesame oil and the BB/oil ratio is set to 8, the time required for releasing about 50% of the total amount of SDE from the formulation into the in vitro medium is about 70-90 minutes (N4); and when the oil used is castor oil and the BB/oil ratio is set to 8, the time required for releasing 50% of the total amount of SDE from the formulation into the in vitro medium is about 120-140 minutes (N13).

It can be seen from FIG. 15 that the dissolution profiles of the N2 and N14 formulations are quite similar though the dissolution rate can be further decreased by using castor oil to replace sesame oil. This pattern is also seen with the comparison between N4 and N13 formulations. This is to say that to replace sesame oil by another pharmaceutical acceptable oil in the present formulation will not significantly affect the correlation between the release period and the BB/oil ratio, i.e., the higher BB/oil ratio, the longer the release period of the formulation. Furthermore, using castor oil to replace with sesame oil may further prolong the release period of the formulation.

We claim:

1. An extended release pharmaceutical formulation comprising sebacoyl dinalbuphine ester (SDE), benzyl benzoate, and sesame oil, wherein:
   the weight ratio of the benzyl benzoate to the sesame oil is greater than 1 and less than 19;
   the concentration of the SDE in the formulation is from about 50 to about 150 mg/mL;
   the formulation is a homogeneous solution substantially free of solid particles and suitable for administration to a human subject by intramuscular injection; and
   the mean whole blood concentration of nalbuphine is at least about 1 ng/mL at 12 hours after intramuscular administration of a single dose of the formulation to human subjects.

2. The extended release pharmaceutical formulation of claim 1, wherein the mean whole blood concentration of nalbuphine is at least about 3 ng/mL at 24 hours after intramuscular administration of a single dose of the formulation to human subjects.

3. The extended release pharmaceutical formulation of claim 1, wherein the mean whole blood concentration of nalbuphine is at least about 3 ng/mL at 48 hours after intramuscular administration of a single dose of the formulation to human subjects.

4. The extended release pharmaceutical formulation of claim 1, wherein the mean whole blood concentration of nalbuphine is at least about 3 ng/mL at 60 hours after intramuscular administration of a single dose of the formulation to human subjects.

5. The extended release pharmaceutical formulation of claim 1, wherein the mean whole blood concentration of nalbuphine is at least about 3 ng/mL at 72 hours after intramuscular administration of a single dose of the formulation to human subjects.

6. The extended release pharmaceutical formulation of claim 1, wherein the mean whole blood concentration of nalbuphine is at least about 3 ng/mL at 96 hours after intramuscular administration of a single dose of the formulation to human subjects.

7. The extended release pharmaceutical formulation of claim 1, wherein the mean whole blood concentration of nalbuphine is at least about 3 ng/mL at 120 hours after intramuscular administration of a single dose of the formulation to human subjects.

8. The extended release pharmaceutical formulation of claim 1, wherein the mean whole blood concentration of nalbuphine is at least about 1 ng/mL from 24 to 216 hours after intramuscular administration of a single dose of the formulation to human subjects.

9. The extended release pharmaceutical formulation of claim 1, wherein the mean whole blood concentration of nalbuphine is at least about 3 ng/mL from 38 to 132 hours after intramuscular administration of a single dose of the formulation to human subjects.

10. The extended release pharmaceutical formulation of claim 1, wherein the mean apparent elimination half-life ($T_{1/2}$) of nalbuphine is at least about 50 hours after intramuscular administration of a single dose of the formulation to human subjects.

11. The extended release pharmaceutical formulation of claim 10, wherein the $T_{1/2}$ of nalbuphine is about 50 to about 115 hours after intramuscular administration of a single dose of the formulation to human subjects.

12. The extended release pharmaceutical formulation of claim 10, wherein the $T_{1/2}$ of nalbuphine is about 55 to about 90 hours after intramuscular administration of a single dose of the formulation to human subjects.

13. The extended release pharmaceutical formulation of claim 10, wherein the $T_{1/2}$ of nalbuphine is about 70 to about 90 hours after intramuscular administration of a single dose of the formulation to human subjects.

14. The extended release pharmaceutical formulation of claim 10, wherein the $T_{1/2}$ of nalbuphine is about 56 hours, ± about 6 hours, after intramuscular administration of a single dose of the formulation to human subjects.

15. The extended release pharmaceutical formulation of claim 14, wherein the $T_{1/2}$ of nalbuphine is about 56 hours after intramuscular administration of a single dose of the formulation to human subjects.

16. The extended release pharmaceutical formulation of claim 10, wherein the $T_{1/2}$ of nalbuphine is about 85 hours, ± about 30 hours, after intramuscular administration of a single dose of the formulation to human subjects.

17. The extended release pharmaceutical formulation of claim 16, wherein the $T_{1/2}$ of nalbuphine is about 85 hours after intramuscular administration of a single dose of the formulation to human subjects.

18. The extended release pharmaceutical formulation of claim 10, wherein the $T_{1/2}$ of nalbuphine is about 90 hours, ± about 25 hours, after intramuscular administration of a single dose of the formulation to human subjects.

19. The extended release pharmaceutical formulation of claim 18, wherein the $T_{1/2}$ of nalbuphine is about 90 hours after intramuscular administration of a single dose of the formulation to human subjects.

20. The extended release pharmaceutical formulation of claim 10, wherein the $T_{1/2}$ of nalbuphine is about 73 hours, ± about 31 hours, after intramuscular administration of a single dose of the formulation to human subjects.

21. The extended release pharmaceutical formulation of claim 20, wherein the $T_{1/2}$ of nalbuphine is about 73 hours after intramuscular administration of a single dose of the formulation to human subjects.

22. The extended release pharmaceutical formulation of claim 1, wherein the mean time to maximum plasma concentration ($T_{max}$) of nalbuphine is at least about 45 hours, ± about 25 hours, after intramuscular administration of a single dose of the formulation to human subjects.

23. The extended release pharmaceutical formulation of claim 22, wherein the $T_{max}$ of nalbuphine is at least about 45 hours after intramuscular administration of a single dose of the formulation to human subjects.

24. The extended release pharmaceutical formulation of claim 1, wherein the mean maximum plasma concentration ($C_{max}$) of nalbuphine is at least about 4 ng/mL after intramuscular administration of a single dose of the formulation to human subjects.

25. The extended release pharmaceutical formulation of claim 1, wherein the $C_{max}$ of nalbuphine is at least about 5 ng/mL after intramuscular administration of a single dose of the formulation to human subjects.

26. The extended release pharmaceutical formulation of claim 24, wherein the $C_{max}$ of nalbuphine is about 4 to about 13 ng/mL after intramuscular administration of a single dose of the formulation to human subjects.

27. The extended release pharmaceutical formulation of claim 24, wherein the $C_{max}$ of nalbuphine is about 5 to about 10 ng/mL after intramuscular administration of a single dose of the formulation to human subjects.

28. The extended release pharmaceutical formulation of claim 1, wherein the single dose of the formulation comprises about 75 mg to about 150 mg of SDE.

29. The extended release pharmaceutical formulation of claim 28, wherein the single dose of the formulation comprises about 150 mg of SDE.

30. The extended release pharmaceutical formulation of claim 1, wherein the weight ratio of the benzyl benzoate to the sesame oil is about 1.1:1.

31. The extended release pharmaceutical formulation of claim 1, wherein the weight ratio of the benzyl benzoate to the sesame oil is about 1.12:1.

32. The extended release pharmaceutical formulation of claim 1, wherein the concentration of the SDE in the formulation is about 75 mg/mL.

33. The extended release pharmaceutical formulation of claim 1, wherein the formulation is prepared by:
  (1) dissolving the SDE in the benzyl benzoate; and
  (2) mixing the resulting solution with the sesame oil to obtain a homogeneous solution.

34. The extended release pharmaceutical formulation of claim 33, wherein the homogeneous solution is sterilized by filtration.

35. The extended release pharmaceutical formulation of claim 1, wherein the formulation does not comprise precipitates or solid particles.

36. The extended release pharmaceutical formulation of claim 1, wherein the formulation remains homogeneous at 2-8° C. for at least 24 months.

37. The extended release pharmaceutical formulation of claim 36, wherein the formulation remains homogenous after one or more freeze-thaw cycles.

* * * * *